US012753178B2

(12) United States Patent
Huang et al.

(10) Patent No.: US 12,753,178 B2
(45) Date of Patent: Oct. 6, 2026

(54) METHODS OF MAKING WEE1 INHIBITOR COMPOUNDS

(71) Applicant: Recurium IP Holdings, LLC, San Diego, CA (US)

(72) Inventors: Peter Qinhua Huang, San Diego, CA (US); Chad Daniel Hopkins, San Diego, CA (US); Brant Clayton Boren, San Diego, CA (US); Sunny Abraham, San Diego, CA (US); Kevin Duane Bunker, Escondido, CA (US); Sobhana Babu Boga, San Diego, CA (US); Shuguang Zhu, San Diego, CA (US); Tao Wu, San Diego, CA (US); Benjamin Pratt, Encinitas, CA (US)

(73) Assignee: Recurium IP Holdings, LLC, San Diego, CA (US)

(*) Notice: Subject to any disclaimer, the term of this patent is extended or adjusted under 35 U.S.C. 154(b) by 694 days.

(21) Appl. No.: 18/001,234

(22) PCT Filed: Jun. 9, 2021

(86) PCT No.: PCT/US2021/036665

§ 371 (c)(1),
(2) Date: Dec. 8, 2022

(87) PCT Pub. No.: WO2021/252667

PCT Pub. Date: Dec. 16, 2021

(65) Prior Publication Data

US 2023/0234956 A1 Jul. 27, 2023

Related U.S. Application Data

(60) Provisional application No. 63/037,766, filed on Jun. 11, 2020.

(51) Int. Cl.
*C07D 487/04* (2006.01)
*C07D 221/04* (2006.01)

(52) U.S. Cl.
CPC ......... *C07D 487/04* (2013.01); *C07D 221/04* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 11,124,518 | B2 | 9/2021 | Huang et al. |
| 11,261,192 | B2 | 3/2022 | Huang et al. |
| 12,410,204 | B2 | 9/2025 | Abraham et al. |
| 2020/0157112 | A1 | 5/2020 | Huang et al. |
| 2021/0139482 | A1 | 5/2021 | Huang et al. |
| 2021/0317124 | A1 | 10/2021 | Huang et al. |
| 2022/0024939 | A1 | 1/2022 | Huang et al. |
| 2023/0002426 | A1 | 1/2023 | Huang et al. |
| 2023/0008362 | A1 | 1/2023 | Samatar et al. |
| 2023/0054854 | A1 | 2/2023 | Samatar et al. |
| 2023/0068370 | A1 | 3/2023 | Samatar et al. |
| 2023/0087941 | A1 | 3/2023 | Samatar et al. |
| 2023/0210854 | A1 | 7/2023 | Samatar et al. |
| 2023/0234956 | A1 | 7/2023 | Huang et al. |
| 2023/0265097 | A1 | 8/2023 | Hopkins et al. |
| 2024/0197743 | A1 | 6/2024 | Pultar et al. |
| 2024/0261295 | A1 | 8/2024 | Donate et al. |
| 2024/0299395 | A1 | 9/2024 | Donate et al. |
| 2024/0325397 | A1 | 10/2024 | Samatar et al. |
| 2024/0325412 | A1 | 10/2024 | Donate et al. |
| 2024/0335447 | A1 | 10/2024 | Donate et al. |
| 2024/0391924 | A1 | 11/2024 | Huang et al. |
| 2024/0408097 | A1 | 12/2024 | Samatar et al. |
| 2025/0205240 | A1 | 6/2025 | Jameson et al. |
| 2025/0208149 | A1 | 6/2025 | Harismendy et al. |
| 2025/0262214 | A1 | 8/2025 | Ma et al. |
| 2025/0262215 | A1 | 8/2025 | Chung et al. |
| 2026/0028363 | A1 | 1/2026 | Abraham et al. |

FOREIGN PATENT DOCUMENTS

| | | |
|---|---|---|
| WO | WO 2016/081290 | 5/2016 |
| WO | WO 2016/181290 | 11/2016 |
| WO | WO 2018/075937 | 4/2018 |
| WO | WO 2019/028008 | 2/2019 |
| WO | WO 2019/173082 | 9/2019 |
| WO | WO 2020/210320 | 10/2020 |
| WO | WO 2021/097139 | 5/2021 |
| WO | WO 2021/127039 | 6/2021 |
| WO | WO 2021/127044 | 6/2021 |
| WO | WO 2021/127045 | 6/2021 |
| WO | WO 2021/127047 | 6/2021 |

(Continued)

OTHER PUBLICATIONS

Anelli et al. J. Org. Chem. 1987, 52, 2559-2562 (Year: 1987).*
Xie et al. Tetrahedron: Asymmetry 20, 2009. 1425-1432 (Year: 2009).*
Klapars and Buchwald, J. Am. Chem. Soc. 2002, 124, 14844-14845 (Year: 2002).*
International Preliminary Report on Patentability issued Dec. 13, 2022 for PCT Application No. PCT/US2021/036665, filed Jun. 9, 2021.
Office Action dated Jun. 9, 2023 for Russian Application No. 2022132321, filed Jun. 9, 2021.

(Continued)

*Primary Examiner* — Kortney L. Klinkel
*Assistant Examiner* — Donna M Nestor
(74) *Attorney, Agent, or Firm* — Knobbe, Martens, Olson & Bear, LLP

(57) ABSTRACT

A process is provided for making a WEE1 inhibitor of the formula (1A) useful in the treatment of conditions characterized by excessive cellular proliferation, such as cancer. In some embodiments, processes are provided for making intermediate compounds of the formulae (3), (5) and (6) as defined herein.

20 Claims, 13 Drawing Sheets

(56) References Cited

FOREIGN PATENT DOCUMENTS

| | | |
|---|---|---|
| WO | WO 2021/231653 | 11/2021 |
| WO | WO 2021/252667 | 12/2021 |
| WO | WO 2022/011391 | 1/2022 |
| WO | WO 2022/136916 | 6/2022 |
| WO | WO 2022/221143 | 10/2022 |
| WO | WO 2022/251224 | 12/2022 |
| WO | WO 2022/271731 | 12/2022 |
| WO | WO 2023/064282 | 4/2023 |
| WO | WO 2023/076485 | 5/2023 |
| WO | WO 2023/114871 | 6/2023 |
| WO | WO 2023/114875 | 6/2023 |
| WO | WO 2023/114877 | 6/2023 |
| WO | WO 2024/031048 | 2/2024 |
| WO | WO 2024/059696 | 3/2024 |
| WO | WO 2024/059808 | 3/2024 |
| WO | WO 2024/102649 | 5/2024 |
| WO | WO 2024/102650 | 5/2024 |
| WO | WO 2024/249756 | 12/2024 |
| WO | WO 2025/076311 | 4/2025 |
| WO | WO 2025/106635 | 5/2025 |
| WO | WO 2025/179038 | 8/2025 |
| WO | WO 2025/184572 | 9/2025 |
| WO | WO 2025/188946 | 9/2025 |
| WO | WO 2025/193930 | 9/2025 |
| WO | WO 2025/226653 | 10/2025 |
| WO | WO 2025/231223 | 11/2025 |

OTHER PUBLICATIONS

International Search Report and Written Opinion mailed Aug. 11, 2021 for PCT Application No. PCT/US2021/036665.

Partial European Search Report dated Sep. 25, 2023 for EP Application No. 21821961.6, filed Jun. 9, 2021.

Extended European Search Report dated Jan. 4, 2024 for EP Application No. 21821961.6, filed Jun. 9, 2021.

Office Action dated Dec. 5, 2024 for Russian Application No. 2022132321, filed Jun. 9, 2021.

Asahara et al., Solvent Handbook, Kodansha Ltd. (1985) pp. 47-51.

Ashizawa et al., The Science of Polymorphism and Crystallization of Pharmaceuticals, Maruzen Planet Co., Ltd. (Sep. 2002) pp. 305-317.

Caira, M.R., "Crystalline polymorphism of organic compounds" Topics in Current Chemistry, Springer Verlag Berlin Heidelberg (1998) 198 pp. 163-208.

Deryabina et al., Workshop in Organic Chemistry, Part I, Methods of Purification and Identification of Organic Compounds, Univers-Group Publishing House (2005) in 83 pages, Section 2.2 "Crystallization", pp. 35-39.

Hirayama, N., Organic Compound Crystallization Handbook—Principles and Know-How, Maruzen Co., Ltd., (2008) pp. 36-43.

Kawaguchi et al., Journal of Human Environmental Engineering (2002) 4(2):310-317.

Klapars, et al., "Copper-Catalyzed Halogen Exchange in Aryl Halides: An Aromatic Finkelstein Reaction", Journal of the American Chemical Society (2002) 124(50):14844-14845 and Supporting Information.

Matsuoka, M., Fundamentals and Applications of Crystal Polymorphism, Popular Edition, 1st Edition, CMC Publishing Co., Ltd. (Oct. 2010) pp. 105-117 and 181-191.

Rodríguez-Spong et al.: "General principles of pharmaceutical solid polymorphism: a supramolecular perspective" Adv. Drug Deliv. Rev. (2004) 56(3):241-274.

Sarma et al., "Solid formation of pharmaceuticals: Polymorphs, salt and cocrystals" Korean J. Chem. Eng. (2011) 28(2):315-322.

Takada, N., "API Form screening and selection in drug discovery stage" Pharm Stage, (Jan. 2007) (10):20-25.

The Fifth Series of Experimental Chemistry Basics I, Fundamentals of Experiments and Information, edited by The Chemical Society of Japan, Maruzen Co., Ltd. (Sep. 2003) pp. 162-166.

Yamano, M., "Approach to Crystal Polymorph in Process Research of New Drug", Journal of the Society of Synthetic Organic Chemistry Japan (Sep. 2007) 65(9):907-913.

Office Action dated Aug. 10, 2025 for Israeli Application No. 298971, filed Jun. 9, 2021.

Office Action mailed Mar. 11, 2025 for Japanese Application No. 2022-576010, filed Jun. 9, 2021.

Rejection Decision mailed Aug. 26, 2025 for Japanese Application No. 2022-576010, filed Jun. 9, 2021.

Office Action dated Jun. 9, 2025 for Russian Application No. 2022132321, filed Jun. 9, 2021.

Office Action and Search Report dated Feb. 8, 2025 for TW Application No. 110121419, filed Jun. 11, 2021.

Aldridge, S., "The shape shifters" Chem. World (2007):64-70.

Karpinski, P., "Polymorphism of Active Pharmaceutical Ingredients" Chem. Eng. Technol. (2006) 29(2):233-237.

Laird, T., "Polymorphism—Still Unpredictable" Org. Proc. Res. Dev. (2010) 14(1):1.

Xie et al., "Design and synthesis of new chiral pyridine-phosphite ligands for the cooper-catalized enantioselective conjugate addition of diethylzinc to acyclic enones" Tetrahedron: Asymmetry (2009) 20:1425-1432.

Examination Report dated Feb. 17, 2026 for Indian Application No. 202217076306, filed Jun. 9, 2021.

Office Action dated Dec. 15, 2025 for Korean Application No. 10-2023-7001260, filed Jun. 9, 2021.

Office Action dated Dec. 5, 2025 for Russian Application No. 2022132321, filed Jun. 9, 2021.

Rejection Decision dated Sep. 25, 2025 for TW Application No. 110121419, filed Jun. 11, 2021.

* cited by examiner

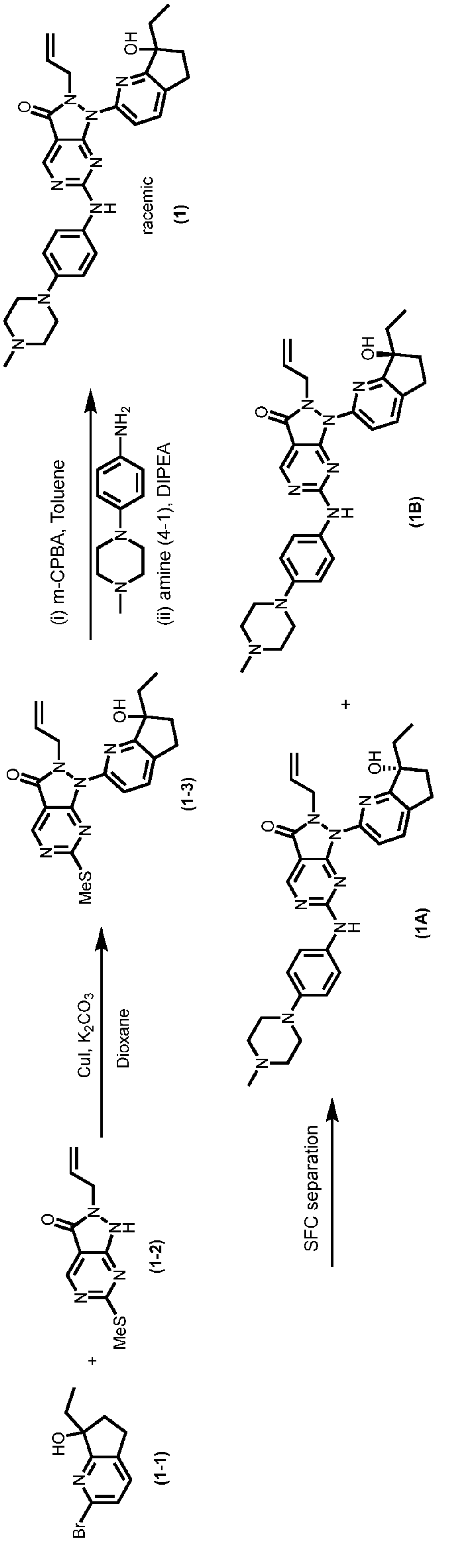
FIG. 1 (Prior Art WO 2019/173082)

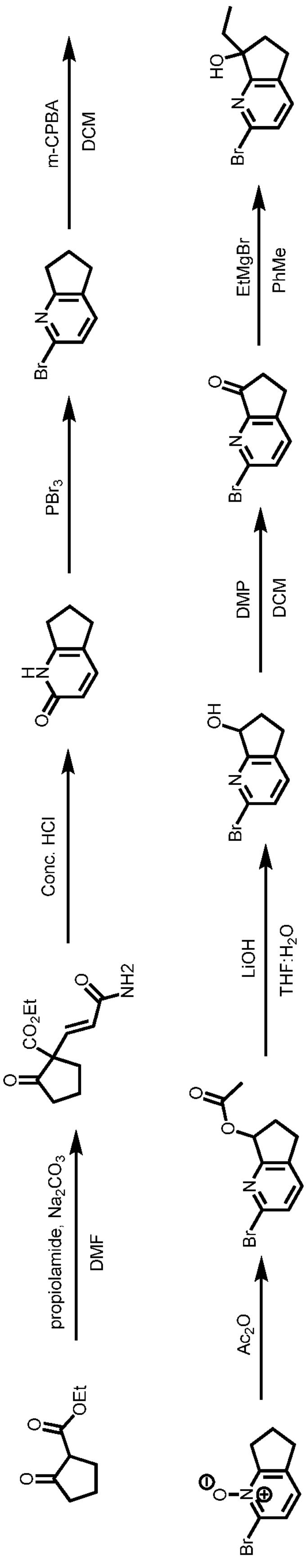
(1-1)
FIG. 2 (Prior Art WO 2019/173082)

(3-1) + (3-2) → (3)

(3-1) + (3-2) → (3)

(3) (1A)

(3) (1A)

(5-1) (5-2) (5)

(5-1) (5-2) (5)

(5) (6)

(5) (6)

(7-1) (7-2) (7-3) (7-4)

(7-5) (7-6) (7-7) (7)

(3-2) (8-1) (7) (3) (1A)

(7)

(8-1)

(3-2)

(3)

(1A)

METHODS OF MAKING WEE1 INHIBITOR COMPOUNDS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57 including U.S. Provisional Application No. 63/037,766, filed Jun. 11, 2020.

BACKGROUND

Field

The present application relates to methods of making compounds that are WEE1 inhibitors, which are used to treat conditions characterized by excessive cellular proliferation, such as cancer.

Background

WEE1 kinase plays a role in the G2-M cell-cycle checkpoint arrest for DNA repair before mitotic entry. Normal cells repair damaged DNA during G1 arrest. Cancer cells often have a deficient G1-S checkpoint and depend on a functional G2-M checkpoint for DNA repair. WEE1 is overexpressed in various cancer types.

PCT Publication WO 2019/173082 discloses a variety of WEE1 inhibitors and methods of making them, including a synthetic route as illustrated in FIG. 1 for making the following racemic compound (1):

(1)

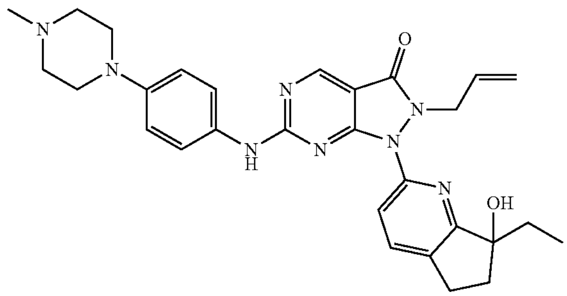

PCT Publication WO 2019/173082 also discloses resolution of the racemic compound (1) by SFC chromatography as indicated in FIG. 1 to form the following enantiomers (1A) and (1B):

(1A)

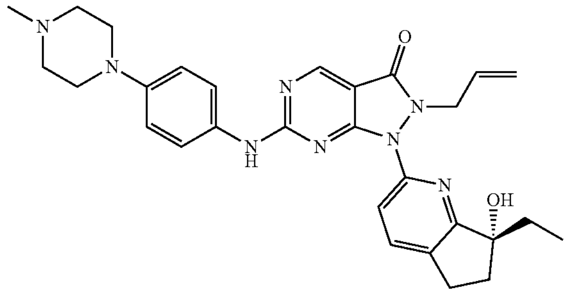

-continued (1B)

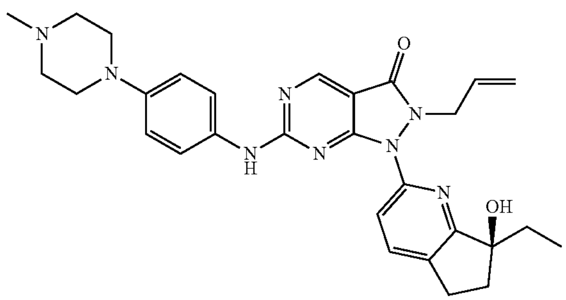

The method described in PCT Publication WO 2019/173082 for making such enantiomers (1A) and (1B) represents a substantial advance in the art. However, in practice the method has proven to be challenging to scale up and overall yields are low, due at least in in part to the presence of multiple reaction steps and the use of SFC chromatography for separation of the enantiomers. For example, the racemic starting compound (1-1) used to make compound (1) is difficult to obtain from commercial sources. It is described in PCT Publication WO 2019/173082 as having been prepared in low overall yield by a multi-step reaction scheme as illustrated in FIG. 2. Additional challenges relate to the desire for chiral products to be highly enantiopure. Thus, there remains a need for further advances in the art of making enantiomers (1A) and (1B).

SUMMARY

A number of improvements in methods of making the WEE1 inhibitor of the formula (1A) have now been developed that are much more practical for scale up and manufacturing as compared to the methods described in PCT Publication WO 2019/173082.

An embodiment provides a compound of the formula (3) that is useful in the production of the WEE1 inhibitor of the formula (1A), for example as illustrated in FIGS. 4A and 4B.

Another embodiment provides a method of making the compound of formula (3), comprising reacting a compound of the formula (3-1) with a compound of the formula (3-2) under Ullman coupling reaction conditions effective to form the compound of formula (3), for example as illustrated in FIGS. 3A and/or 3B. In various embodiments, the variable X in formula (3-1) is Cl, Br or I.

Another embodiment provides a method of making the compound of formula (1A), comprising oxidizing the compound of the formula (3) under reaction conditions effective to form an oxidized intermediate; and reacting the oxidized intermediate with an amine compound of the formula (4-1) under reaction conditions effective to form the compound of formula (1A), for example as illustrated in FIGS. 4A and/or 4B.

Another embodiment provides a method of making a compound of the formula (5), comprising: reacting a compound of the formula (5-1) with acetic anhydride under reaction conditions effective to form an acetyl intermediate of the formula (5-2); and reacting the acetyl intermediate of the formula (5-2) with a hydroxide base under reaction conditions effective to form the compound of formula (5), for example as illustrated in FIGS. 5A and 5B. In various embodiments, the variable X in formulae (5-1), (5-2) and (5) is Cl, Br or I.

Another embodiment provides a method of making a compound of the formula (6), comprising reacting a compound of the formula (5) with an oxidizing agent under oxidizing reaction conditions effective to form the compound of formula (6), for example as illustrated in FIGS. 6A and 6B. In various embodiments, the variable X in formulae (5) and (6) is Cl, Br or I.

These and other embodiments are described in greater detail below.

BRIEF DESCRIPTION OF THE DRAWINGS

FIG. 1 illustrates a prior art method of making compounds of the formulae (1A) and (1B) utilizing the compound of formula (1-1) as a starting material.

FIG. 2 illustrates a prior art method of making the compound of formula (1-1).

DETAILED DESCRIPTION

An embodiment provides a compound of the following formula (3):

(3)

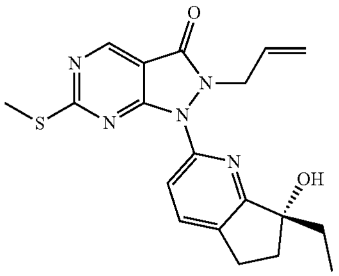

Figure 4A:
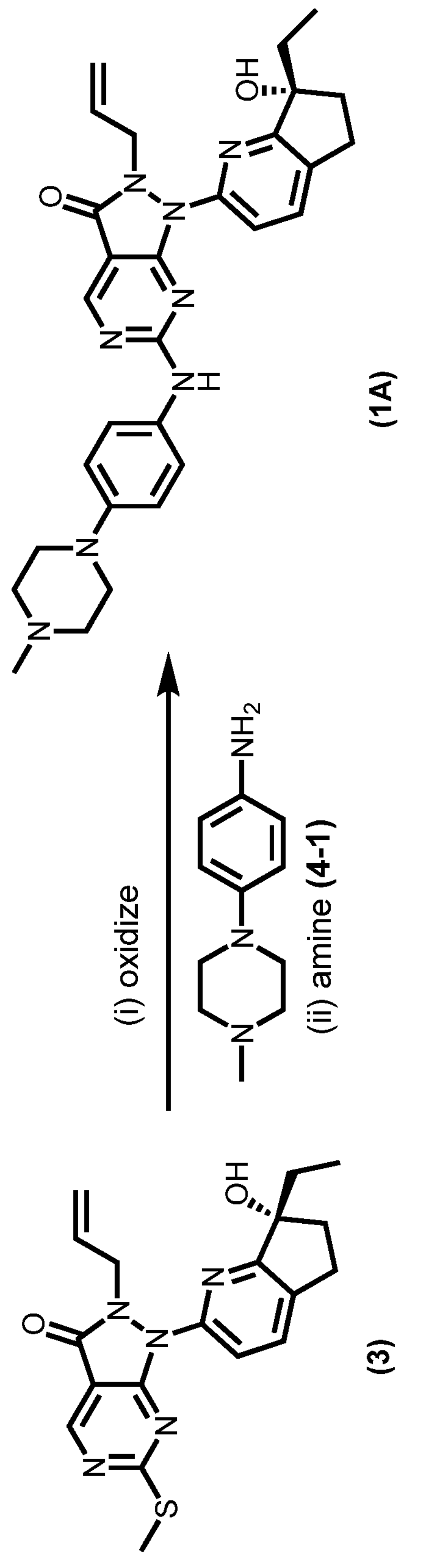
FIG. 4A illustrates an embodiment of a method of making a compound of the formula (1A).
Figure 4B:
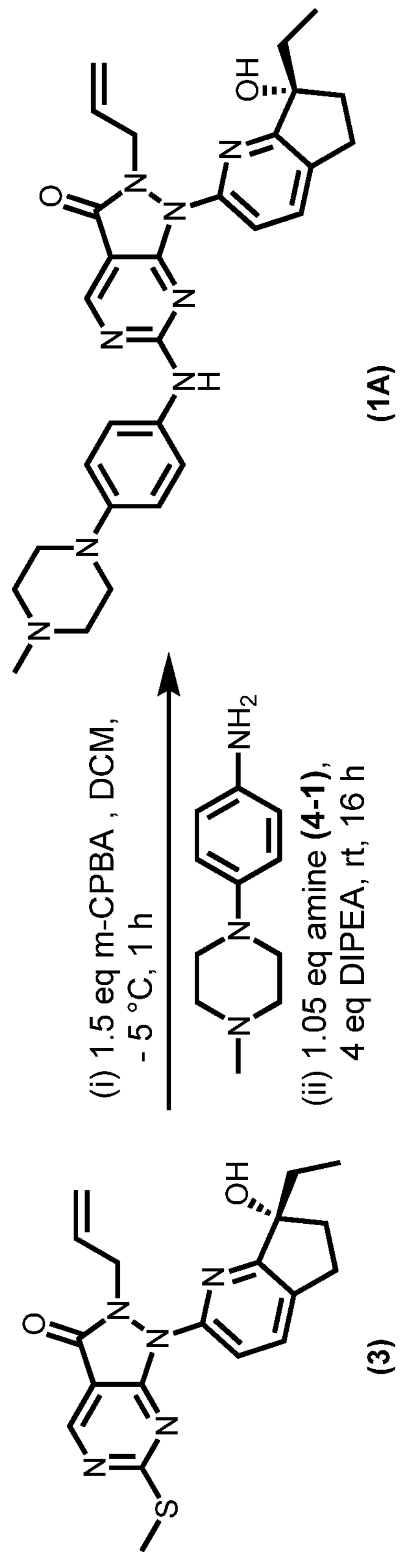
FIG. 4B illustrates an embodiment of a method of making a compound of the formula (1A).

The compound of formula (3) is an enantiomer that is useful in the production of the WEE1 inhibitor of the formula (1A) as illustrated in FIGS. 4A and 4B. In various embodiments, the compound of formula (3) is highly enantiopure as indicated by an enantiomeric excess (ee) value of at least about 85%, 90%, 95% or 97%.

The compound of formula (3) can be made in various ways. For example, an embodiment provides a method of making the compound of formula (3), comprising reacting a compound of the following formula (3-1) with a compound of the following formula (3-2) under Ullman coupling reaction conditions effective to form the compound of formula (3):

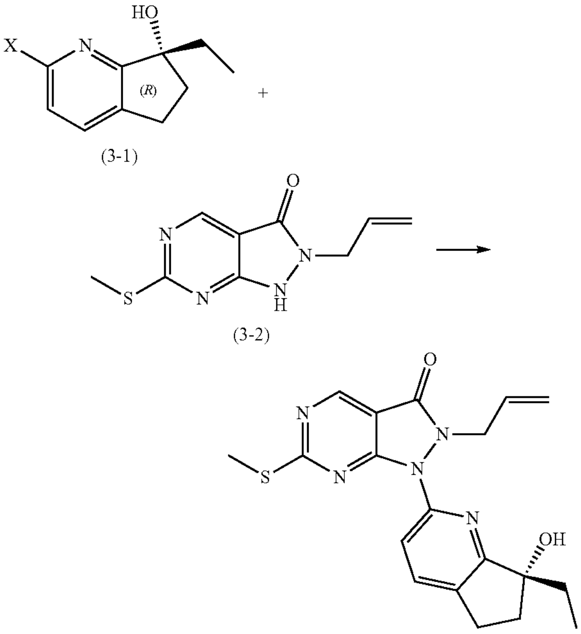

(3-1) + (3-2) → (3)

Figure 3A:
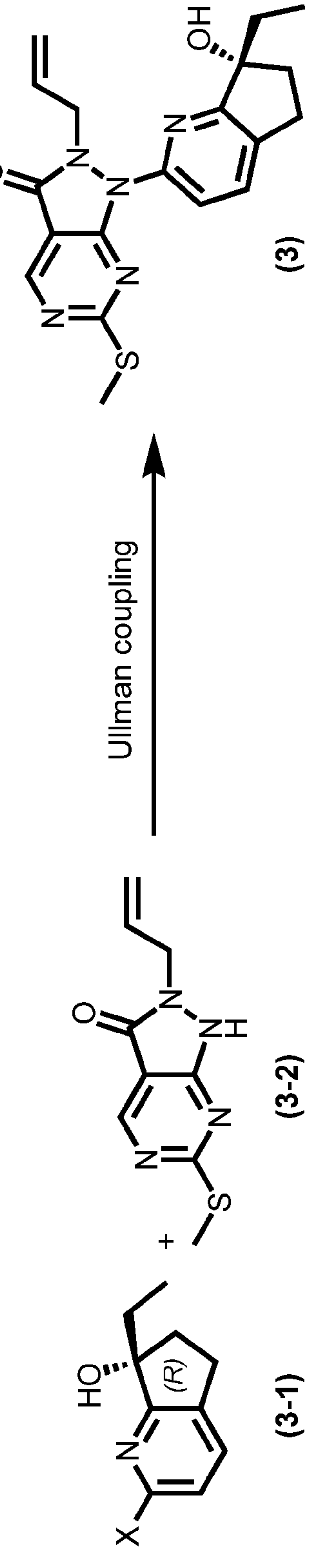
FIG. 3A illustrates an embodiment of a method of making a compound of the formula (3).
Figure 3B:
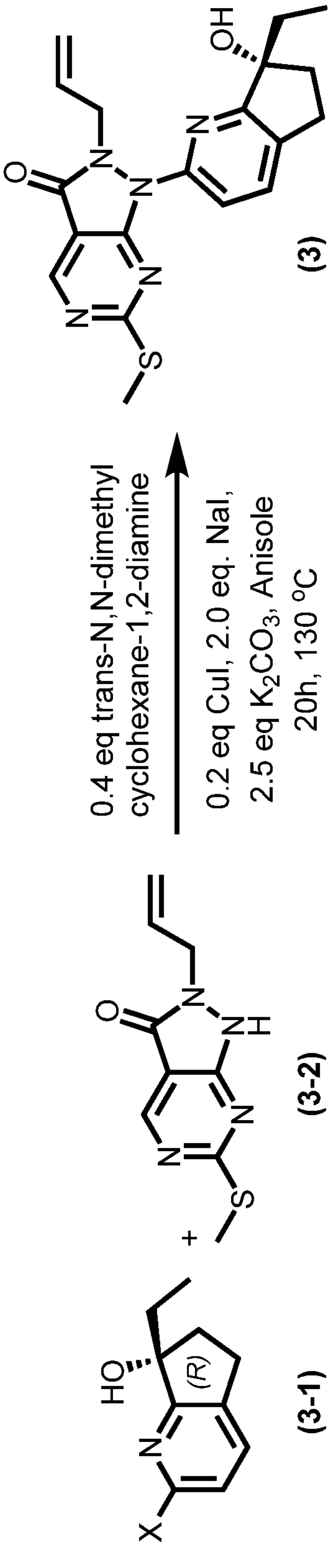
FIG. 3B illustrates an embodiment of a method of making a compound of the formula (3).

In various embodiments, the variable X in formula (3-1) is Cl, Br or I. For example, in an embodiment, the variable X in formula (3-1) is Cl. Those skilled in the art recognize that in this context the term "Ullman coupling reaction conditions" refers to a copper-mediated amination reaction that forms a carbon-nitrogen (C—N) bond between the pyridinyl ring of the compound of formula (3-1) and the secondary amine of the compound of formula (3-2) as illustrated in FIG. 3A. Those skilled in the art are aware of various Ullman coupling reaction conditions that utilize a copper-mediated amination reaction to couple an amine with an aryl or alkenyl electrophile in the presence of copper and a base to form a new C—N bond. Those skilled in the art can readily adapt such known Ullman coupling reaction conditions for use in the preparation of compound (3) using routine experimentation guided by the present disclosure.

In various embodiments, the Ullman coupling reaction conditions comprise reacting the compound of the formula (3-1) and the compound of the formula (3-2) together in the presence of an effective amount of a copper salt and/or Cu(0). Examples of suitable copper salts include CuI, CuBr, CuCl and combinations thereof. Examples of suitable sources of Cu(0) include elemental copper. The copper salt or Cu(0) may be used in combination with an inorganic salt such as NaI, NaBr, NaCl, KI, KBr, KCl or a combination thereof. In an embodiment, the Ullman coupling reaction conditions comprise reacting the compound of the formula (3-1) and the compound of the formula (3-2) together in the presence of an effective amount of CuI and, optionally, an effective amount of NaI.

In various embodiments, the Ullman coupling reaction conditions comprise reacting the compound of the formula (3-1) and the compound of the formula (3-2) together in the presence of an effective amount of a polar aprotic solvent. Various polar aprotic solvents may be used. For example, in an embodiment, the polar aprotic solvent comprises dioxane, anisole, 1,2-dimethoxyethane (glyme), diethylene glycol dimethyl ether (diglyme), dimethyl acetamide, 1-methylpyrrolidin-2-one, or a combination thereof. In an embodiment, the polar aprotic solvent consists of or comprises anisole.

In various embodiments, the Ullman coupling reaction conditions comprise reacting the compound of the formula (3-1) and the compound of the formula (3-2) together in the presence of an effective amount of a chelating ligand. Various chelating ligands known to those skilled in the art may be used. In an embodiment, the chelating ligand comprises trans-N,N-dimethylcyclohexane-1,2-diamine, N,N-dimethylethane-1,2-diamine, 2,2'-bypyridyl, N,N'-dibenzylethane-1,2-diamine, trans-1,2-diaminocyclohexane or a combination thereof. For example, in an embodiment, the chelating ligand comprises trans-N,N-dimethylcyclohexane-1,2-diamine.

In various embodiments, the Ullman coupling reaction conditions comprise reacting the compound of the formula (3-1) and the compound of the formula (3-2) together in the presence of an effective amount of an inorganic base. Various inorganic bases known to those skilled in the art may be used. In an embodiment, the inorganic base comprises $K_2CO_3$, $K_3PO_4$, $Cs_2CO_3$, $Na_2CO_3$ or a combination thereof. For example, in an embodiment the inorganic base comprises $K_2CO_3$.

In various embodiments, the Ullman coupling reaction conditions comprise reacting the compound of the formula (3-1) and the compound of the formula (3-2) together in the presence of effective amounts of a polar aprotic solvent, a chelating ligand, a copper salt, an inorganic base and, optionally, an iodide salt. For example, in an embodiment, the Ullman coupling reaction conditions comprise the presence of effective amounts of a polar aprotic solvent, a chelating ligand, CuI, NaI, and an inorganic base. FIG. 5B illustrates an example of such Ullman coupling reaction conditions.

In various embodiments, the Ullman coupling reaction conditions comprise reacting the compound of the formula (3-1) and the compound of the formula (3-2) together for a reaction time in the range of 2 to 40 hours. In an embodiment, the Ullman coupling reaction conditions comprise a reaction time in the range of 4 to 36 hours, for example, a reaction time of about 4, 6, 8, 10, 12, 14, 16, 18, 20, 22, 24, 26, 28, 30, 32, 34 or 36 hours, or a reaction time within a range defined by endpoints selected from any two of the aforementioned reaction time values.

In various embodiments, the Ullman coupling reaction conditions comprise reacting the compound of the formula (3-1) and the compound of the formula (3-2) together at an elevated reaction temperature. In an embodiment, the Ullman coupling reaction conditions comprise a reaction temperature in the range of about 70° C. to about 150° C., for example, a reaction temperature of about 70° C., 75° C., 80° C., 85° C., 90° C., 95° C., 100° C., 105° C., 110° C., 115° C., 120° C., 125° C., 130° C., 135° C., 140° C., 145° C. or 150° C., or a reaction temperature within a range defined by endpoints selected from any two of the aforementioned reaction temperature values.

In various embodiments, the method of making the compound of formula (3) is carried out as illustrated in FIGS. 3A and/or 3B.

In some embodiments, a solid form of Compound 3 can be characterized by one or more peaks in an X-ray powder diffraction pattern selected from:

| °2-θ | d(Å) | Relative Intensity |
|---|---|---|
| 8.6 | 10.21 | 100 |
| 11.5 | 7.69 | 11.5 |
| 17.3 | 5.09 | 26.6 |
| 23.2 | 3.83 | 15.7 |

Figure 9:
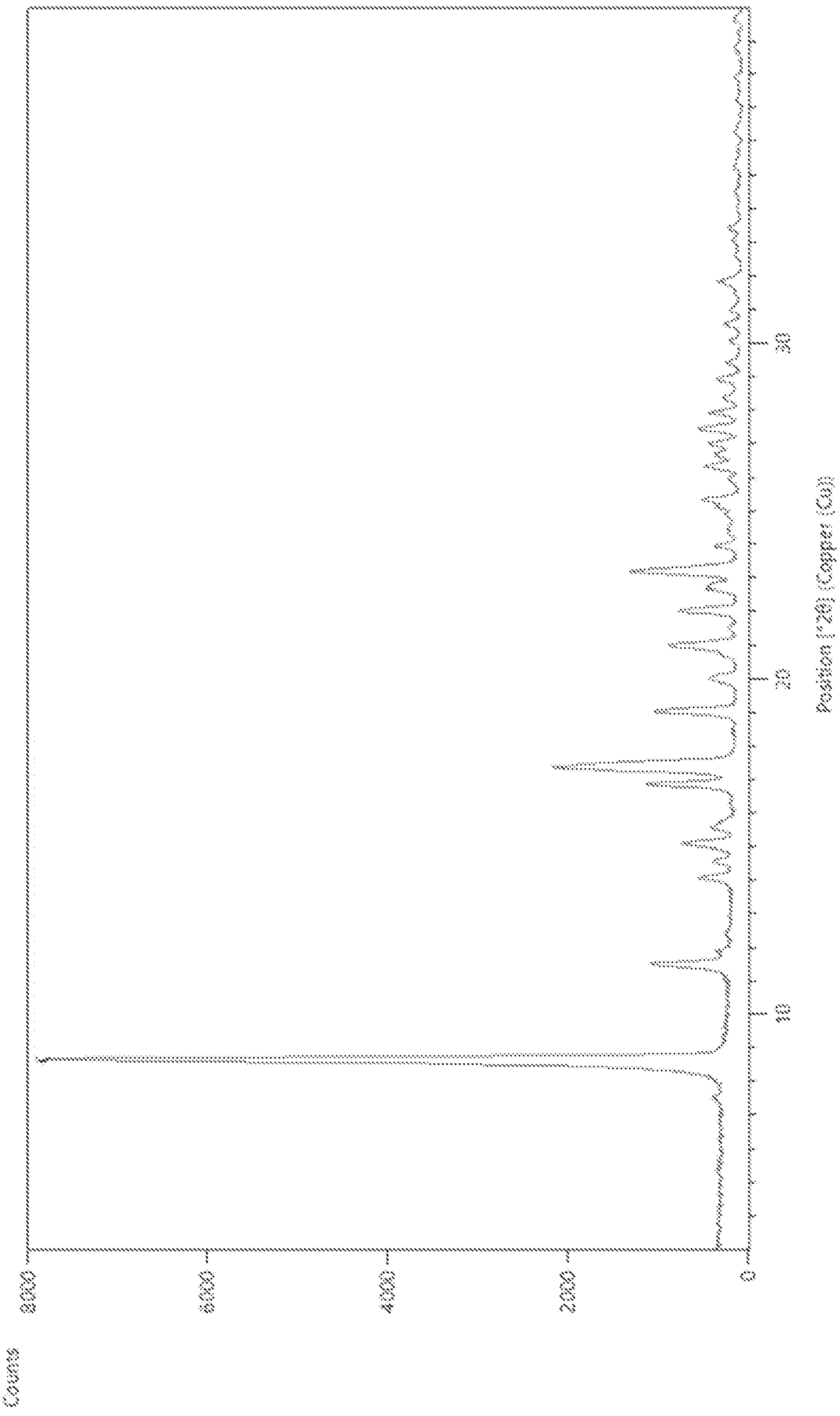
FIG. 9 provides a representative X-ray powder diffraction (XRPD) pattern of Compound 3.

In some embodiments, a solid form of Compound 3 can be characterized by one or more peaks in an XRPD pattern, wherein the one or more peaks can be selected from a peak in the range from 8.8 degrees to about 8.4 degrees 2θ, 11.7 degrees to about 11.3 degrees 2θ, 17.5 degrees to about 17.1 degrees 2θ and 23.4 degrees to about 23.0 degrees 2θ. In some embodiments, a solid form of Compound 3 can be characterized by one or more peaks in an X-ray powder diffraction pattern, wherein the one or more peaks can be selected from about 8.6 degrees 2θ±0.2 degrees 2θ, about 11.5 degrees 2θ±0.2 degrees 2θ, about 17.3 degrees 2θ±0.2 degrees 2θ and about 23.2 degrees 2θ±0.2 degrees 2θ. In some embodiments, a solid form of Compound 3 can exhibit an X-ray powder diffraction pattern as shown in FIG. 9.

Figure 10:
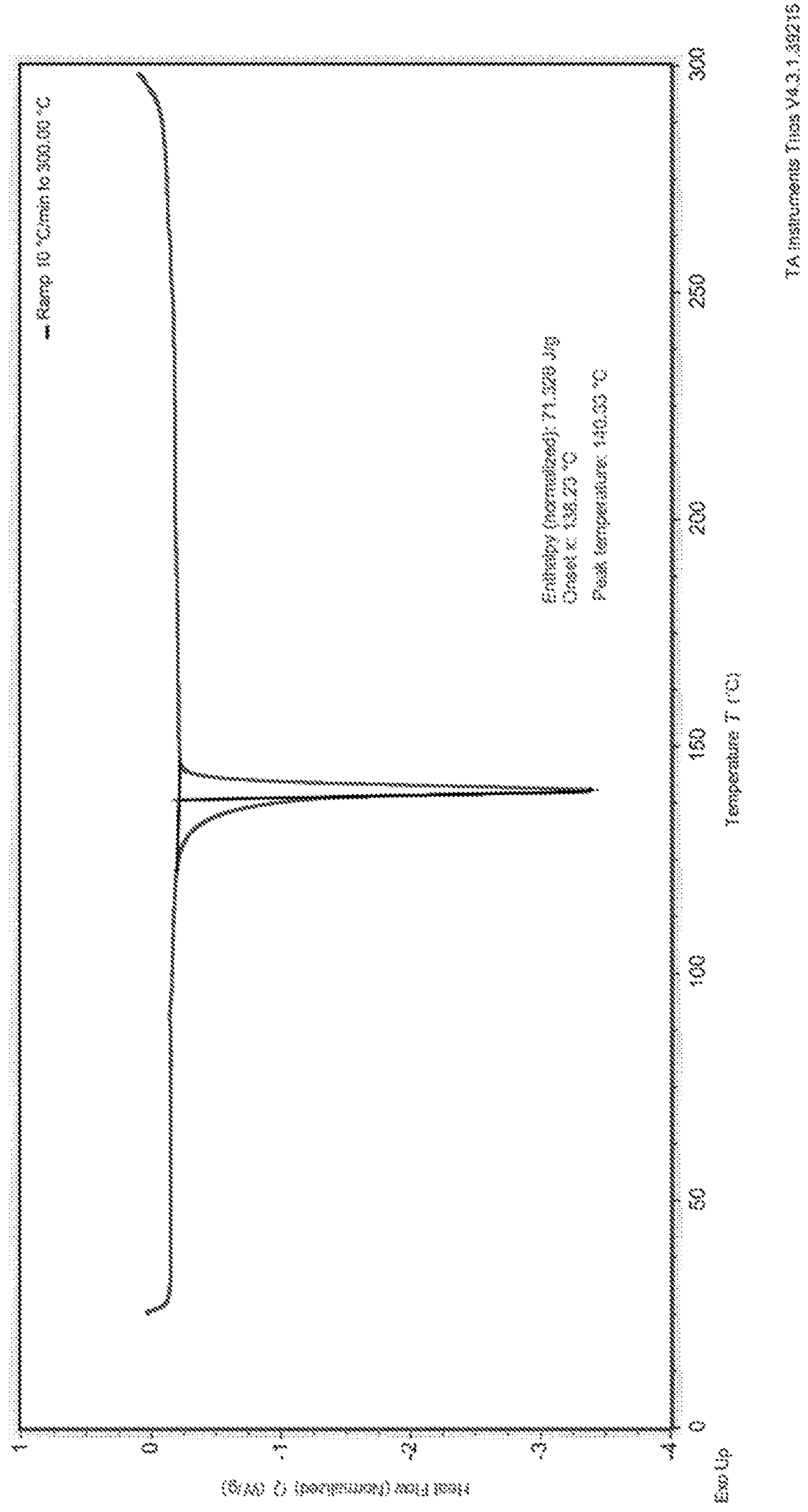
FIG. 10 provides a representative DSC thermogram of Compound 3.

In some embodiments, a solid form of Compound 3 can be characterized by an endotherm in the range of about 135° C. to about 145° C. In some embodiments, a solid form of Compound 3 can be characterized by a differential scanning calorimetry (DSC) thermogram comprising an exotherm peak at about 140° C. In some embodiments, a solid form of Compound 3 can have a differential scanning calorimetry (DSC) thermogram of FIG. 10.

Figure 11:
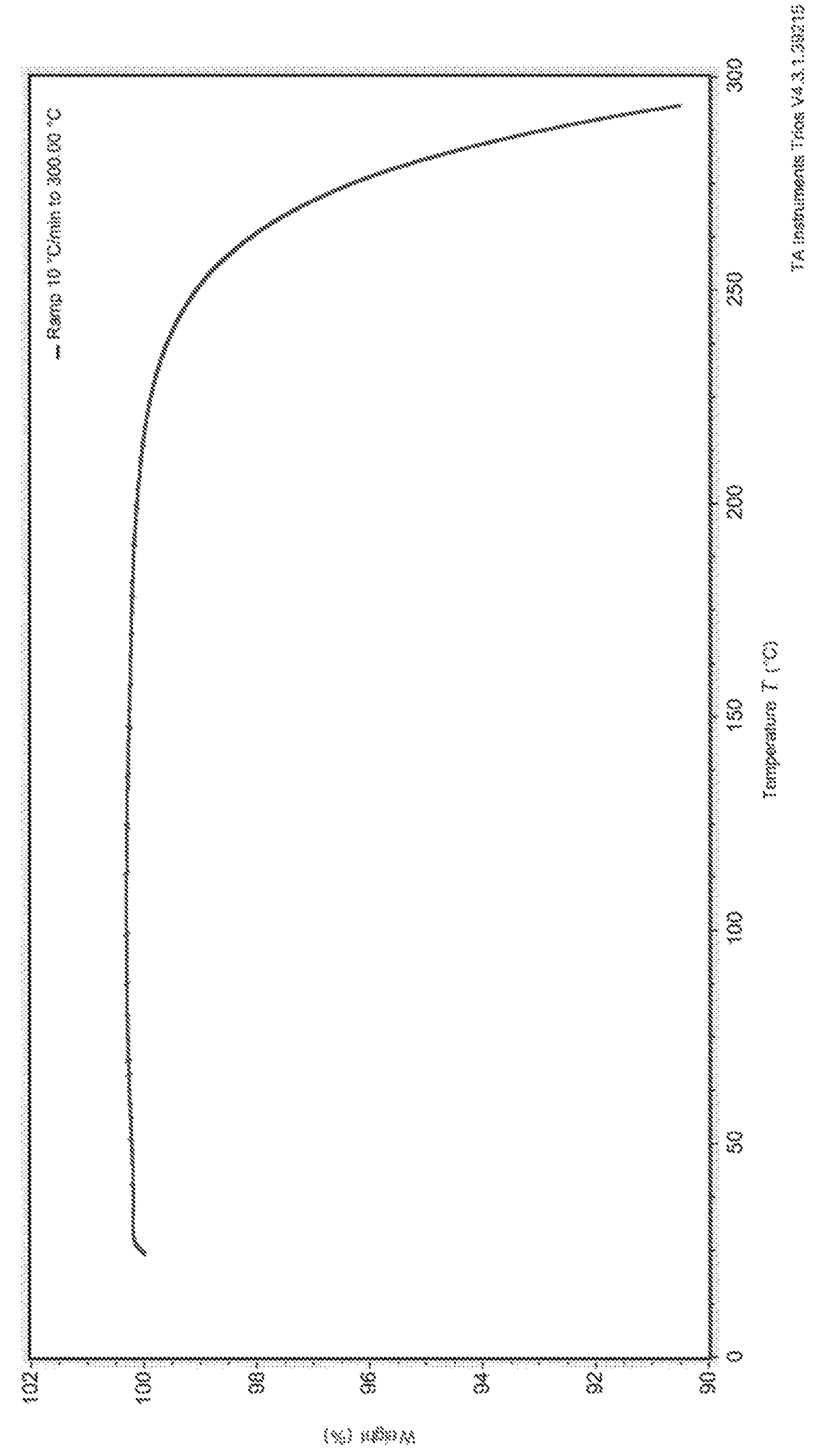
FIG. 11 provides a representative TGA thermogram of Compound 3.

In some embodiments, a solid form of Compound 3 can have a weight loss percent in the range of about 0% to about 2% when heated from about 40° C. to about 150° C. In some embodiments, a solid form of Compound 3 can have a weight loss percent of about 0% when heated from about 40° C. to about 150° C. In some embodiments, a solid form of Compound 3 can be characterized by the TGA curves depicted in FIG. 11.

Another embodiment provides a method of making the compound of formula (1A), comprising:

oxidizing the compound of the formula (3) under reaction conditions effective to form an oxidized intermediate; and reacting the oxidized intermediate with an amine compound of the following formula (4-1) under reaction conditions effective to form the compound of formula (1A):

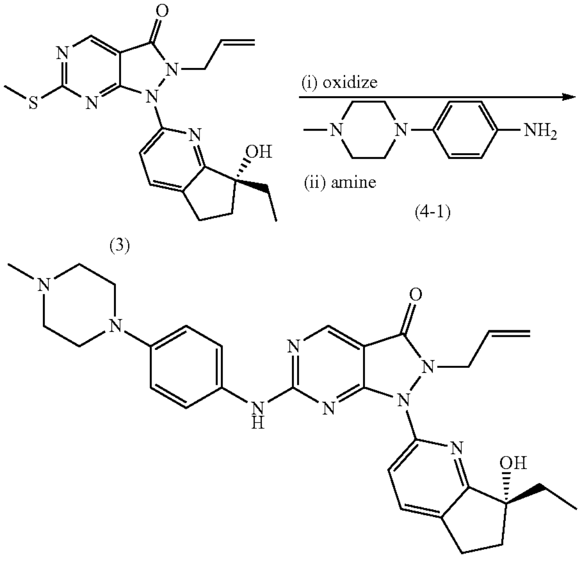

(3) (4-1)

(1A)

In various embodiments, the reaction conditions effective to form the oxidized intermediate comprise oxidizing the compound of the formula (3) by reacting with an effective amount of an oxidizing agent. The oxidized intermediate (not illustrated in FIG. 4A or 4B) need not be isolated and those skilled in the art may infer its existence or presence from knowledge of the reaction conditions.

Various oxidizing agents known to those skilled in the art may be used. In various embodiments, the oxidizing agent is selected from oxone, m-chloroperbenzoic acid (MCPBA), $H_2O_2$, $Na_2WO_4$, NaOCl, cyanuric acid, $NaIO_4$, $RuCl_3$, $O_2$, or a combination thereof. In an embodiment, the oxidizing agent is oxone, MCPBA or a combination thereof. In an embodiment, the oxidizing agent is oxone. In an embodiment, the oxidizing agent is MCPBA.

In various embodiments, the reaction conditions effective to form the oxidized intermediate comprise oxidizing the compound of the formula (3) in the presence of an effective amount of an organic solvent. Various organic solvents that are effective for dissolving the compound of the formula (3) and the oxidizing agent may be used. In an embodiment, the solvent is a low boiling point chlorinated $C_{1-3}$ hydrocarbon such as chloroform or dichloromethane (DCM). In some embodiments, the solvent comprises water, ethanol, 1-Methyl-2-pyrrolidone, dimethylformamide, tetrahydrofuran, 2-methyltetrahydrofuran, acetonitrile, bis(2-butoxyethyl)ether, bis(2-ethoxyethyl)ether, bis(2-methoxyethyl) ether, dioxane, or a combination of thereof.

In various embodiments, the reaction conditions effective to form the oxidized intermediate comprise a reaction time in the range of 30 minutes to 60 hours. In some embodiments, the reaction conditions effective to form the oxidized intermediate comprise a reaction time in the range of 30 minutes to 48 hours, for example, a reaction time of about 0.5, 1, 2, 4, 6, 8, 10, 12, 14, 16, 18, 20, 22, 24, 26, 28, 30, 32, 34, 36, 38, 40, 42, 44, 46 or 48 hours, or a reaction time within a range defined by endpoints selected from any two of the aforementioned reaction time values.

In various embodiments, the reaction conditions effective to form the oxidized intermediate comprise a relatively low reaction temperature. In an embodiment, the reaction conditions effective to form the oxidized intermediate comprise a reaction temperature in the range of about −25° C. to about 25° C., for example, a reaction temperature of about −25° C., −20° C., −15° C., −10° C., −5° C., 0° C., 5° C., 10° C., 15° C., 20° C., or 25° C., or a reaction temperature within a range defined by endpoints selected from any two of the aforementioned reaction temperature values.

In various embodiments, the reaction conditions effective to react the oxidized intermediate with the amine compound of the formula (4-1) to form the compound of formula (1A) comprise the presence of an effective amount of a base (e.g., an organic base or an inorganic base). Various bases known to those skilled in the art may be used. In an embodiment, the base is an inorganic base. For example, in an embodiment, the inorganic base is selected from $K_2CO_3$, $Na_2CO_3$, $NaHCO_3$, NaOAc or a combination thereof. In an embodiment, the base is an organic base, such as an organic base that comprises a tertiary amine. For example, in an embodiment, the organic base comprises N,N-diisopropylethylamine (DIPEA), triethylamine (TEA), 1,8-Diazabicyclo[5.4.0]undec-7-ene (DBU), or a combination thereof.

In various embodiments, the reaction conditions effective to form the compound of formula (1A) comprise a reaction time in the range of 2 minutes to 40 hours. In some embodiments, the reaction conditions effective to form the compound of formula (1A) comprise a reaction time in the range of 4 hours to 36 hours, for example, a reaction time of about 4, 6, 8, 10, 12, 14, 16, 18, 20, 22, 24, 26, 28, 30, 32 34, or 36 hours, or a reaction time within a range defined by endpoints selected from any two of the aforementioned reaction time values.

In various embodiments, the reaction conditions effective to form the compound of formula (1A) comprise a relatively moderate reaction temperature. In an embodiment, the reaction conditions effective to form the compound of formula (1A) comprise a reaction temperature in the range of about 0° C. to about 50° C., for example, a reaction temperature of about 0° C., 5° C., 10° C., 15° C., 20° C., 25° C., 30° C., 35° C., 40° C., 45° C. or 50° C., or a reaction temperature within a range defined by endpoints selected from any two of the aforementioned reaction temperature values.

In various embodiments, the method of making the compound of formula (1A) is carried out as illustrated in FIGS. 4A and/or 4B.

Other embodiments provide methods and compounds useful for making the compound of formula (3-1). For example, an embodiment provides a method of making a compound of the following formula (5), comprising:

reacting a compound of the following formula (5-1) with acetic anhydride under reaction conditions effective to form an acetyl intermediate of the following formula (5-2); and reacting the acetyl intermediate of the formula (5-2) with a hydroxide base under reaction conditions effective to form the compound of formula (5):

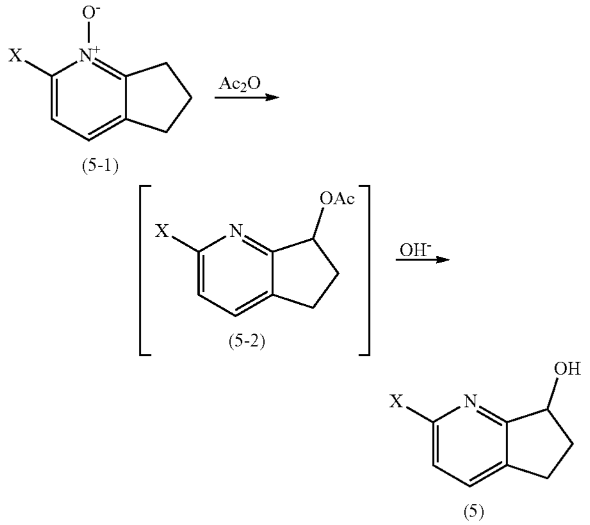

(5-1)

(5-2)

(5)

In various embodiments, the variable X in formula (5-1), (5-2) and (5) is Cl, Br or I. In an embodiment, X is Cl. The acetyl intermediate of the formula (5-2) need not be isolated and those skilled in the art may infer its existence or presence from knowledge of the reaction conditions.

In various embodiments, the reaction conditions effective to form the acetyl intermediate of the formula (5-2) comprise reacting the compound of the formula (5-1) with acetic anhydride in the presence of an effective amount of an organic solvent. Various organic solvents that are effective for dissolving the compound of the formula (5-1) and the acetic anhydride may be used. In various embodiments, the organic solvent comprises acetonitrile ($CH_3CN$), dioxane, toluene, tetrahydrofuran (THF), 2-methyltetrahydrofuran (2-MeTHF), DCM, 1,2-dichoroethane (1,2-DCE), a $C_{1-6}$ alcohol (e.g., methanol, ethanol), or a combination thereof. In an embodiment, the reaction conditions effective to form the compound of formula (5) comprise reacting the compound of the formula (5-1) with acetic anhydride in the presence of an organic solvent that comprises acetonitrile, a $C_{1-6}$ alcohol or a combination thereof. For example, in an embodiment, the organic solvent comprises a $C_{1-6}$ alcohol such as ethanol. In another embodiment, the organic solvent comprises acetonitrile. In other embodiments, the acetic anhydride reactant is used in an excess amount that functions as a solvent, alone or in combination with an organic solvent.

In various embodiments, the reaction conditions effective to form the acetyl intermediate of the formula (5-2) comprise a reaction time in the range of 30 minutes to 12 hours. In some embodiments, the reaction conditions effective to form the acetyl intermediate of the formula (5-2) comprise a reaction time in the range of 30 minutes to 10 hours, for example, a reaction time of about 1, 2, 3, 4, 5, 6, 7, 8, 9 or 10 hours, or a reaction time within a range defined by endpoints selected from any two of the aforementioned reaction time values.

In various embodiments, the reaction conditions effective to form the acetyl intermediate of the formula (5-2) comprise a relatively moderate reaction temperature. In an embodiment, the reaction conditions effective to form the acetyl intermediate of the formula (5-2) comprise a reaction temperature in the range of about 60° C. to about 130° C., for example, a reaction temperature of about 60° C., 65° C., 70° C., 75° C., 80° C., 85° C., 90° C., 95° C., 100° C., 105° C., 110° C., 115° C., 120° C., 125° C. or 130° C., or a reaction temperature within a range defined by endpoints selected from any two of the aforementioned reaction temperature values.

In some embodiments the acetyl intermediate of the formula (5-2) is not isolated but is instead reacted in situ with a hydroxide base under reaction conditions effective to form the compound of the formula (5). Various hydroxide bases known to those skilled in the art may be used. In various embodiments, the hydroxide base is selected from LiOH, NaOH, KOH, $Mg(OH)_2$, $Ca(OH)_2$ and combinations thereof. For example, in an embodiment, the hydroxide base comprises LiOH.

In various embodiments, the reaction conditions effective to form the compound of formula (5) comprise reacting the acetyl intermediate of the formula (5-2) with the hydroxide base in the presence of an aqueous solvent that comprises acetonitrile ($CH_3CN$), a $C_{1-6}$ alcohol (e.g., methanol, ethanol or isopropanol) or a combination thereof. For example, in an embodiment, the aqueous solvent comprises an aqueous $C_{1-6}$ alcohol such as aqueous ethanol.

In various embodiments, the reaction conditions effective to form the compound of formula (5) comprise a reaction time in the range of 1 to 30 hours. In some embodiments, the reaction conditions effective to form the compound of formula (5) comprise a reaction time in the range of 2 hours to 24 hours, for example, a reaction time of about 2, 4, 6, 8, 10, 12, 14, 16, 18, 20, 22 or 24 hours, or a reaction time within a range defined by endpoints selected from any two of the aforementioned reaction time values.

In various embodiments, the reaction conditions effective to form the compound of formula (5) comprise a relatively moderate reaction temperature. In an embodiment, the reaction conditions effective to form the compound of formula (5) comprise a reaction temperature in the range of about 0° C. to about 50° C., for example, a reaction temperature of about 0° C., 5° C., 10° C., 15° C., 20° C., 25° C., 30° C., 35° C., 40° C., 45° C., or 50° C., or a reaction temperature within a range defined by endpoints selected from any two of the aforementioned reaction temperature values.

Figure 5A:
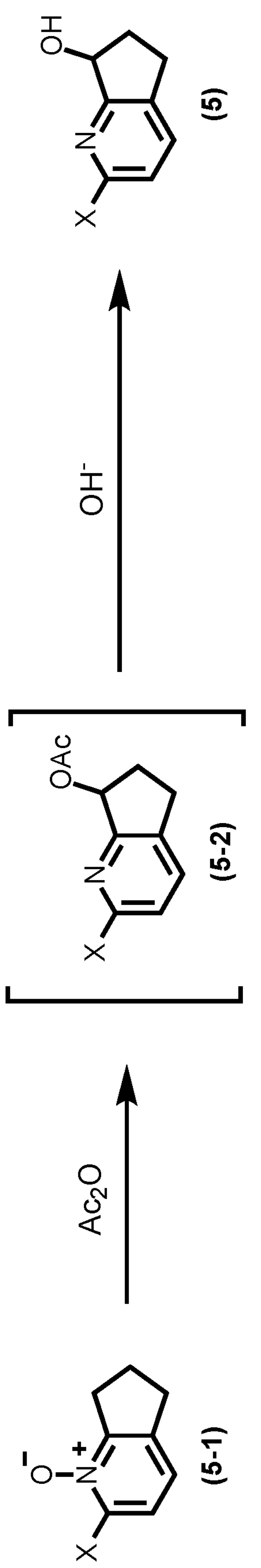
FIG. 5A illustrates an embodiment of a method of making a compound of the formula (5).
Figure 5B:
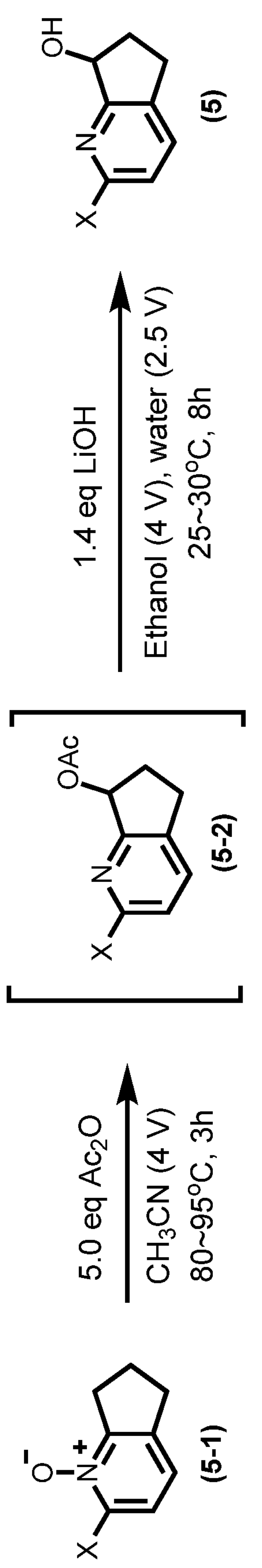
FIG. 5B illustrates an embodiment of a method of making a compound of the formula (5).

In various embodiments, the method of making the compound of formula (5) is carried out as illustrated in FIGS. 5A and/or 5B.

In various embodiments, the compound of the formula (5) is an intermediate that is useful for making another intermediate compound of the formula (6). For example, an embodiment provides a method of making a compound of the following formula (6), comprising reacting a compound of the following formula (5) with an oxidizing agent under oxidizing reaction conditions effective to form the compound of formula (6):

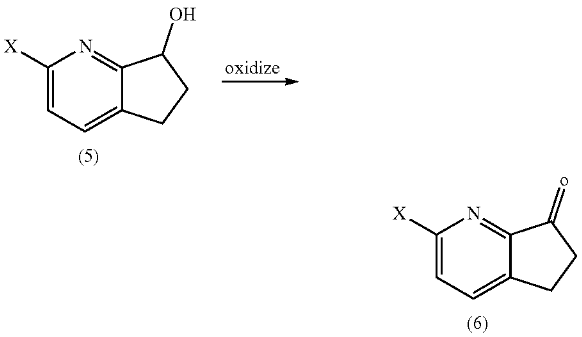

(5)

(6)

In various embodiments, the variable X in formulae (5) and (6) is Cl, Br or I. For example, in an embodiment, the variable X is Cl.

Various oxidizing agents can be used to form the compound of formula (6). In various embodiments, the oxidizing reaction conditions effective to form the compound of formula (6) comprise oxidizing the compound of formula (5) with an effective amount of an oxidizing agent selected from $Na_0Cl$, NaOBr, KOCl, KOBr, $Ca(OCl)_2$ and combinations thereof.

In various embodiments, the oxidizing reaction conditions effective to form the compound of formula (6) comprise mixing the compound of the formula (5) and the oxidizing agent together in a solvent. Various organic solvents that are effective for dissolving the compound of the formula (5) and the oxidizing agent may be used. In an embodiment, the solvent is a low boiling point chlorinated $C_{1-3}$ hydrocarbon such as chloroform or dichloromethane (DCM). In other embodiments, the solvent is water. In some embodiments, the solvent comprises water, methyl acetate, ethyl acetate, isopropyl acetate, acetonitrile, toluene, methyl tert-butyl ether, 2-methyltetrahydrofuran or a combination thereof.

In various embodiments, the oxidizing reaction conditions effective to form the compound of formula (6) comprise mixing the compound of the formula (5) and the oxidizing agent together in the presence of an effective amount of an inorganic base. Various inorganic bases known to those skilled in the art may be used. Examples of suitable inorganic bases include $K_2CO_3$, $Na_2CO_3$ and $NaHCO_3$. In an embodiment, the inorganic base comprises $NaHCO_3$.

The oxidizing reaction conditions effective to form the compound of formula (6) may also include the presence of one or more other additives in amounts effect to facilitate the reaction. In various embodiments, the oxidizing reaction conditions effective to form the compound of formula (6) comprise mixing the compound of the formula (5) and the oxidizing agent together in the presence of an effective amount of (2,2,6,6-tetramethylpiperidin-1-yl)oxidanyl (TEMPO). In some embodiments, the oxidizing reaction conditions effective to form the compound of formula (6) comprise mixing the compound of the formula (5) and the oxidizing agent together in the presence of an effective amount of an inorganic salt. Examples of suitable inorganic salts include LiCl, LiBr, NaCl, NaBr, KCl, KBr, and combinations thereof. In some embodiments, the inorganic salt comprises NaBr.

In various embodiments, the oxidizing reaction conditions effective to form the compound of formula (6) comprise a reaction time in the range of 1 minute to 6 hours. In some embodiments, the oxidizing reaction conditions effective to form the compound of formula (6) comprise a reaction time in the range of 2 minutes to 4 hours, for example, a reaction time of about 2 minutes, 5 minutes, 10 minutes, 30 minutes, 1 hour, 1.5 hours, 2 hours, 2.5 hours, 3 hours, 3.5 hours or 4 hours, or a reaction time within a range defined by endpoints selected from any two of the aforementioned reaction time values.

In various embodiments, the oxidizing reaction conditions effective to form the compound of formula (6) comprise a relatively low reaction temperature. In an embodiment, the oxidizing reaction conditions effective to form the compound of formula (6) comprise a reaction temperature in the range of about −25° C. to about 25° C., for example, a reaction temperature of about −25° C., −20° C., −15° C., −10° C., −5° C., 0° C., 5° C., 10° C., 15° C., 20° C., or 25° C., or a reaction temperature within a range defined by endpoints selected from any two of the aforementioned reaction temperature values.

Figure 6A:
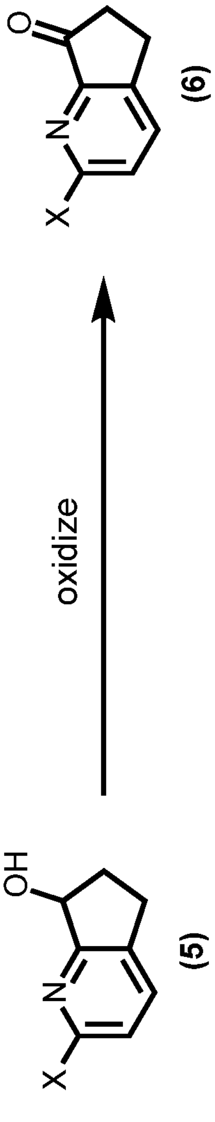
FIG. 6A illustrates an embodiment of a method of making a compound of the formula (6).
Figure 6B:
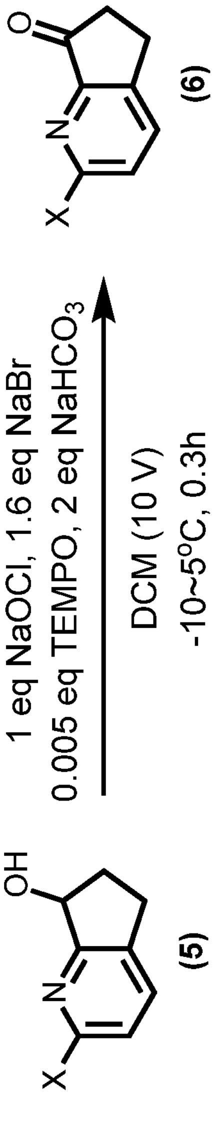
FIG. 6B illustrates an embodiment of a method of making a compound of the formula (6).

In various embodiments, the method of making the compound of formula (6) is carried out as illustrated in FIGS. 6A and/or 6B.

Figure 7A:
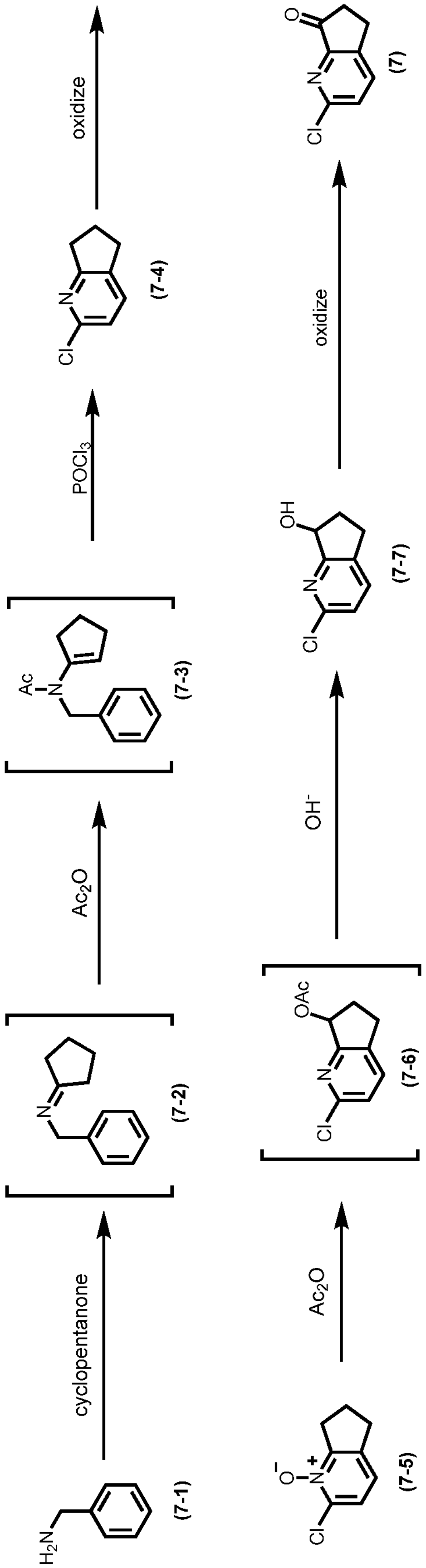
FIG. 7A illustrates an embodiment of a method of making a compound of the formula (7), which is an embodiment of a compound of the formula (6) for which the variable X is Cl.
Figure 7B:
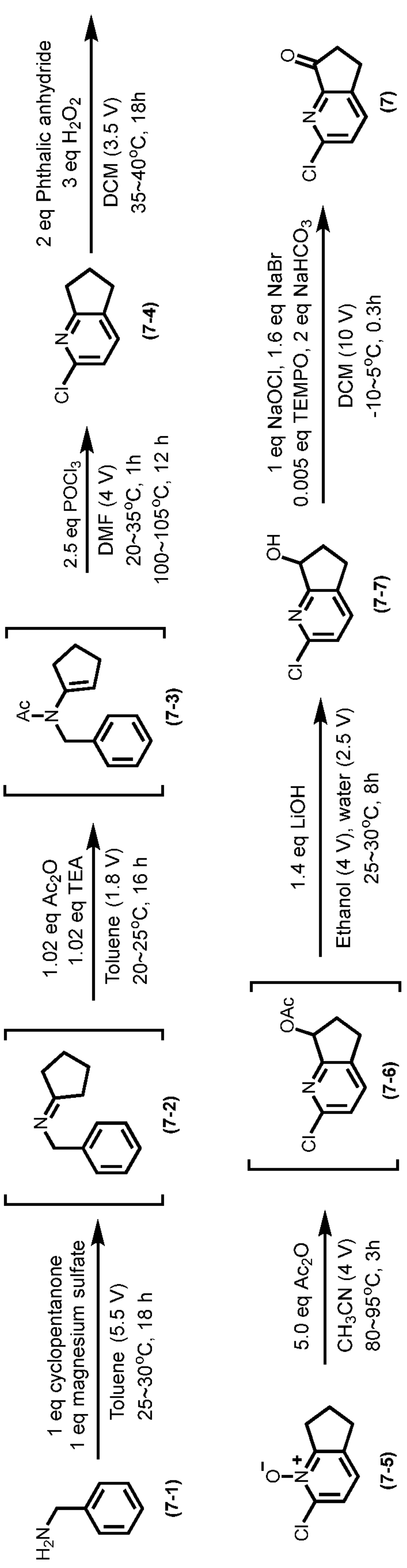
FIG. 7B illustrates an embodiment of a method of making a compound of the formula (7). The compound of the formula (7-7) is an embodiment of the compound of formula (5) for which the variable X is Cl.
Figure 8A:
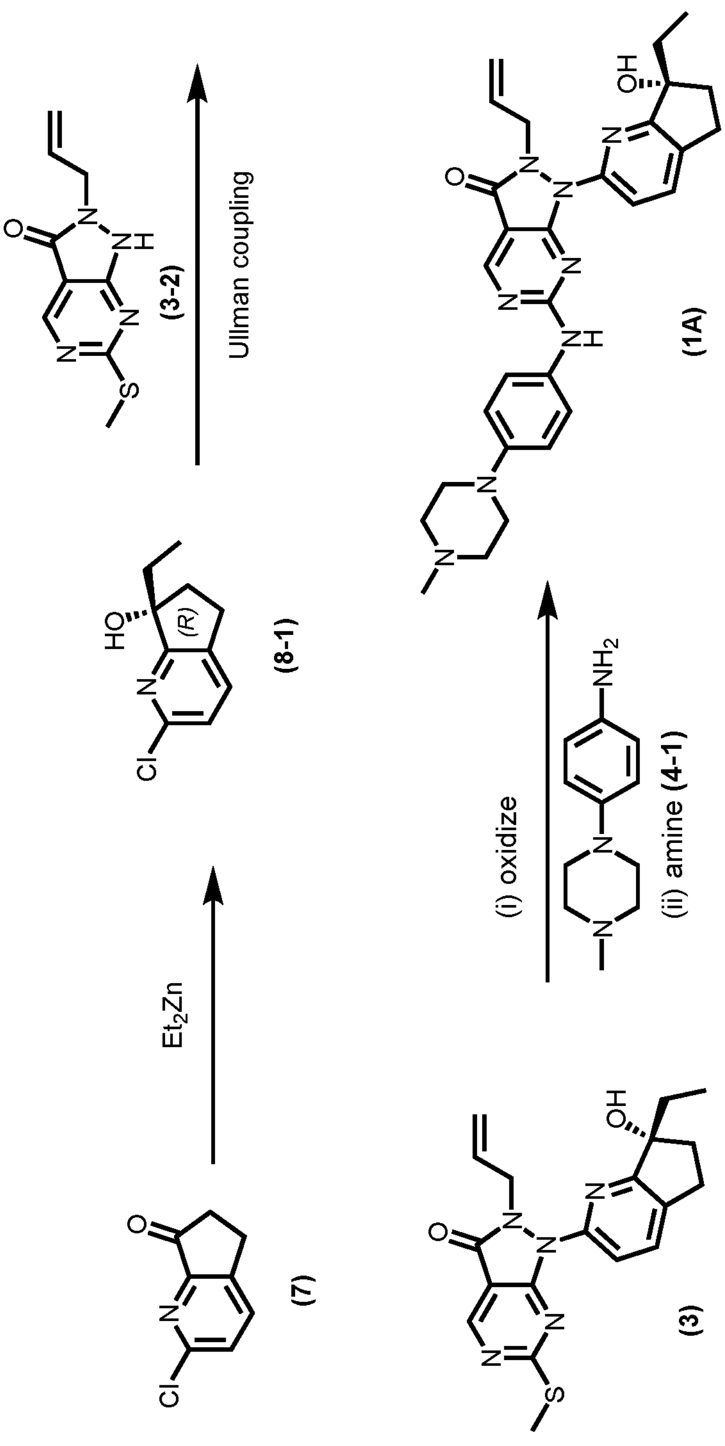
FIG. 8A illustrates an embodiment of a method of making a compound of the formula (1A) utilizing a compound of the formula (7) as a starting material.
Figure 8B:
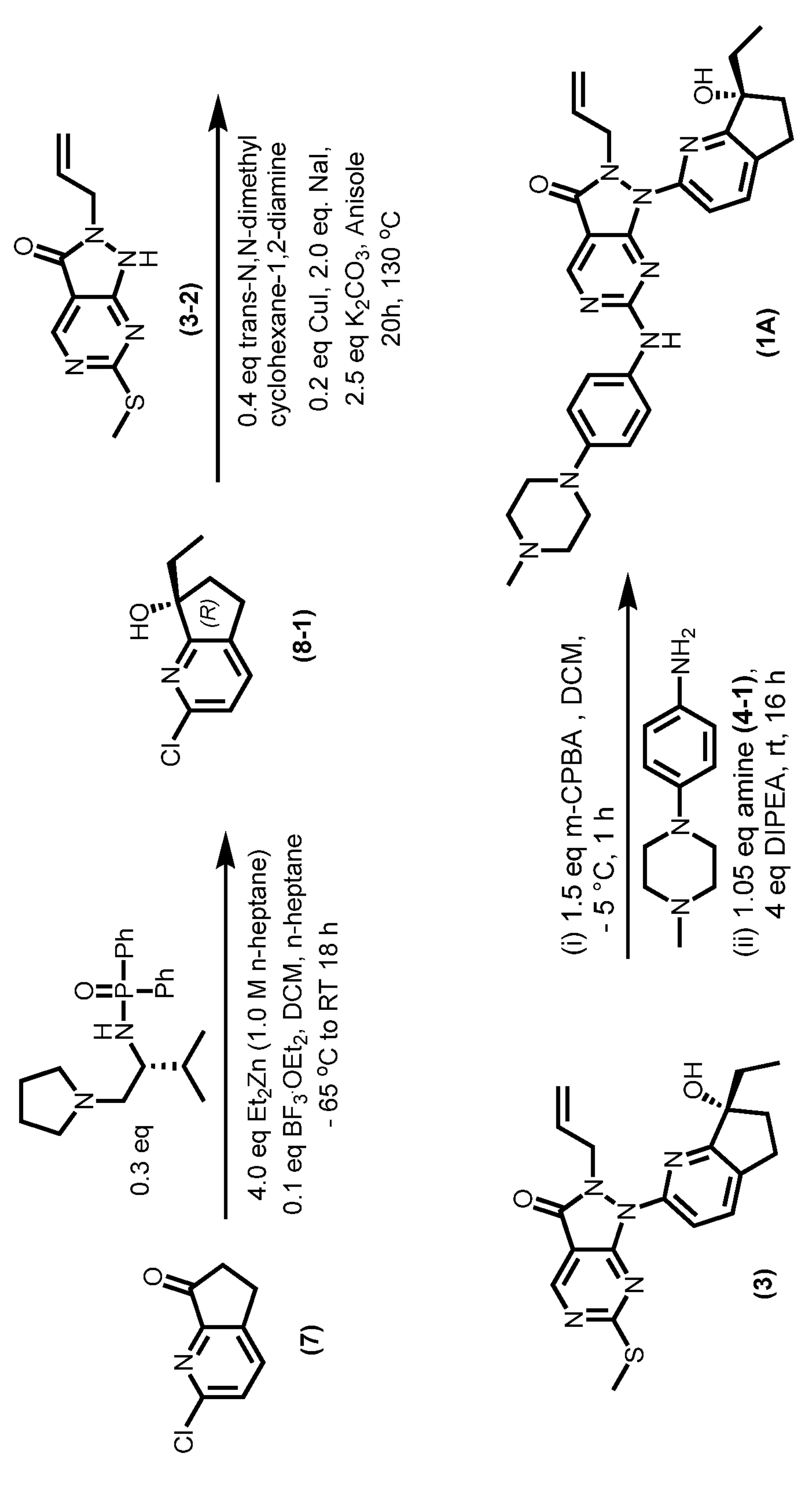
FIG. 8B illustrates an embodiment of a method of making a compound of the formula (1A) utilizing a compound of the formula (7) as a starting material.

The compound of the formula (5) that is used to make the compound of the formula (6) can be made as illustrated in FIGS. 7A and/or 7B. Those skilled in the art will recognize in FIGS. 7A and 7B that the compound of the formula (7-7) is an example of a compound of the formula (5) for which X is Cl. The compound of the formula (6) is useful for making compounds of the formula (3-1), such as the compound (8-1) for which X is Cl as illustrated in FIGS. 8A and 8B. Those skilled in the art will appreciate that FIGS. 7A, 7B, 8A and 8B illustrate other aspects of the present disclosure, including exemplary reaction conditions and embodiments of a method of making a compound of the formula (1A) and a method of making a compound of the formula (3).

Unless otherwise specified, the term "crystalline" and related terms used herein, when used to describe a substance, component, product or form, mean that the substance, component, product or form is substantially crystalline, for example, as determined by X-ray diffraction. (see, e.g., *Remington's Pharmaceutical Sciences,* 20th ed., Lippincott Williams & Wilkins, Philadelphia Pa., 173 (2000); *The United States Pharmacopeia,* 37th ed., 503-509 (2014)).

As used herein, and unless otherwise specified, the terms "about" and "approximately," when used in connection with a numeric value or range of values which is provided to characterize a particular solid form, e.g., a specific temperature or temperature range (for example, that describes a melting, dehydration, desolvation or glass transition temperature); a mass change (for example, a mass change as a function of temperature or humidity); a solvent or water content (for example, mass or a percentage); or a peak position (for example, in analysis by, for example, IR or Raman spectroscopy or XRPD); indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies and dissolution studies. In some embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. In the context of molar ratios, "about" and "approximately" indicate that the numeric value or range of values may vary within 20%, 15%, 10%, 9%, 8%, 7%, 6%, 5%, 4%, 3%, 2%, 1.5%, 1%, 0.5%, or 0.25% of the recited value or range of values. It should be understood that the numerical values of the peaks of an X-ray powder diffraction pattern may vary from one machine to another, or from one sample to another, and so the values quoted are not to be construed as absolute, but with an allowable variability, such as ±0.2 degrees two theta (° 2θ), or more. For example, in some embodiments, the value of an XRPD peak position may vary by up to ±0.2 degrees 2θ while still describing the particular XRPD peak.

EXAMPLES

Additional embodiments are disclosed in further detail in the following examples, which are not in any way intended to limit the scope of the claims.

Example 1

Process Chemistry Route to Compound (1A)

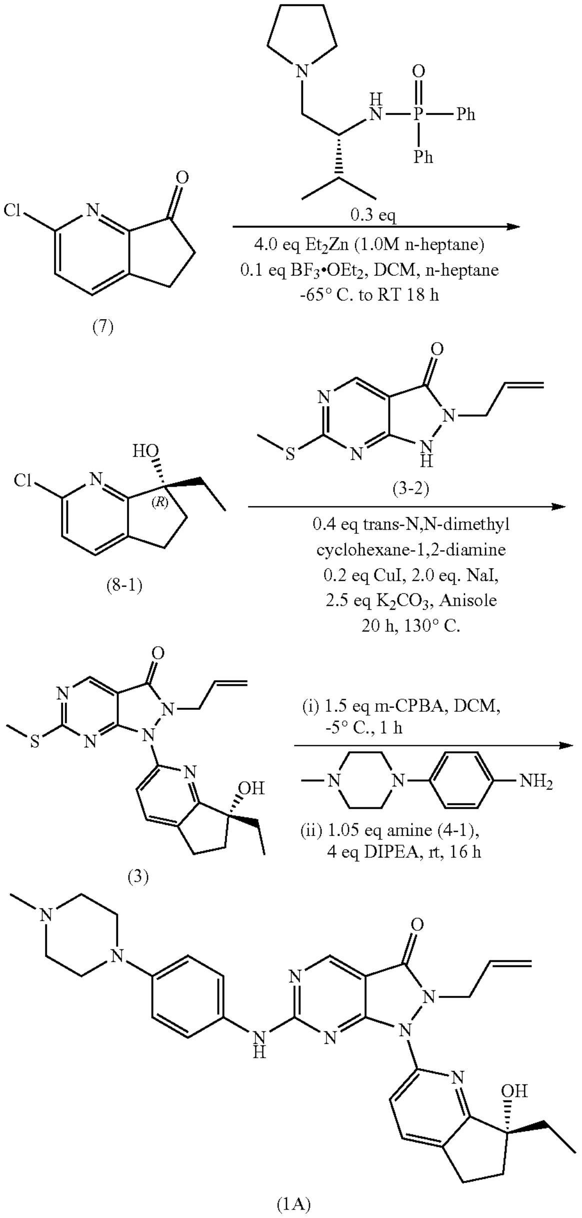

(7)

(3-2)

(8-1)

(3)

(1A)

(R)-2-Chloro-7-ethyl-6,7-dihydro-5H-cyclopenta[b]pyridin-7-ol (compound 8-1): (R)—N-(3-Methyl-1-(pyrrolidin-1-yl)butan-2-yl)-P,P-diphenylphosphinic amide (1276.7 g, 3.580 mol) was suspended in n-heptane (10 L, 5V) in a 100 L glass vessel under $N_2$. The suspension was cooled to an internal temperature of −65° C. 1.0 M diethylzinc in n-heptane (47.76 L, 47.76 mol) was added at the average rate of 0.47 L/min via peristaltic pump. The total addition time was 100 min with a target internal temperature of −52±5° C. The solution was then stirred at −65° C. for 45 min. $BF_3$·$OEt_2$ (169.5 g, 1.19 mol) was added over 10 min with a target internal temperature of −67.5±2.5° C. The mixture was stirred for 60 min at −65° C. where the reaction became a slurry. 2-Chloro-5,6-dihydro-7H-cyclopenta[b]pyridin-7-one (compound 7, 2000 g, 11.94 mol) in DCM (20 L, 10V) was added at a rate of 0.24 L/min via peristaltic pump. The total addition time was 90 min and the internal temperature was maintained at −65±5° C. The solution was stirred for 4 h at −65° C. The temperature was allowed to rise slowly to 20° C. over 17 h, where the reaction was determined to complete by HPLC. The reaction mixture was transferred to another vessel containing saturated $NH_4Cl$ (10 L, 5 V) initially cooled to −5° C. The internal temperature of the quench was maintained between 10 to 25° C. The mixture was filtered, and the residue was washed with 4 L of DCM. The aqueous phase was separated, and the organic layer was washed with water (10 L, 5 V). The combined aqueous layers were extracted with MTBE (10 L, 5 V). The combined organic layers were concentrated to dryness. 2 L of MTBE were added and evaporated to remove DCM. The dark oil was taken up MTBE (5 L, 2.5 V) and passed through a silica plug (10 kg, 5 wt) and washed with the following volumes of n-heptane/MTBE: (10:1, 33 L), (7.5:1, 34 L), (5:1, 54 L), (3:1, 40 L), (2:1, 45 L). The eluent was concentrated under vacuum to give 2.1 kg of compound 8-1 as an oil. The compound was diluted with n-heptane (2 L, 1 V) and heated to 60° C. until all the solids dissolved. The mixture was slowly cooled to 30° C. and a seed crystal (1% wt) was added. The slurry was then cooled to 10° C. and stirred for 1 h. The solids were filtered and dried under a flow of $N_2$ for 16 h to afford compound 8-1 (1.7 kg, 99.8% purity, 92.9% ee) as a beige solid in 72% yield. $^1H$ NMR (400 MHz, $CDCl_3$) δ 7.50 (d, J=7.9 Hz, 1H), 7.17 (d, J=8.1 Hz, 1H), 2.99-2.90 (m, 1H), 2.82-2.71 (m, 1H), 2.33 (ddd, J=4.3, 8.7, 13.4 Hz, 1H), 2.19 (ddd, J=6.8, 9.0, 13.5 Hz, 1H), 2.04-1.89 (m, 1H), 1.81 (qd, J=7.3, 14.1 Hz, 1H), 0.94 (t, J=7.5 Hz, 3H); $^{13}C$ NMR (101 MHz, $CDCl_3$) δ=166.90, 150.07, 135.67, 134.94, 123.10, 81.98, 36.03, 32.37, 26.47, 8.13; LCMS (APCI) 198.1 $[M+H]^+$; 92.9% ee; Chiral analysis was done by LCMS on a Lux Cellulose-4 column (4.6×150 mm), which was eluted by $CH_3CN$/Water 0.1% formic acid at 1.2 mL/min. Under the conditions, compound 8-1 eluted as peak 1 ($t_1$=8.16 min) and the enantiomer was eluted as peak 2 ($t_1$=8.54 min).

(R)-2-Allyl-1-(7-ethyl-7-hydroxy-6,7-dihydro-5H-cyclopenta[b]pyridin-2-yl)-6-(methylthio)-1,2-dihydro-3H-pyrazolo[3,4-d]pyrimidin-3-one (compound 3): To a 20 L reactor were charged compound 8-1 (800 g, 4.05 mol), CuI (153.9 g, 0.81 mol), NaI (1215.2 g, 8.11 mol), $K_2CO_3$ (1397.5 g, 10.13 mol) and 2-allyl-6-(methylthio)-1,2-dihydro-3H-pyrazolo[3,4-cl]pyrimidin-3-one (compound 3-2, 899.2 g, 4.05 mol) and anisole (13.6 L, 17 V). The reactor was flushed with $N_2$ for 30 min. The reactor was charged with trans-N,N'-dimethylcyclohexane-1,2-diamine (230.1 g, 1.62 mol). The reaction was stirred at 130° C. for 20 h where it was determined to be complete by HPLC. The reaction was cooled to 25° C. for 2 h and filtered. The filter cake was washed with anisole (1600 mL, 2V) and MTBE (2400 mL, 3 V). The combined filtrates were washed with a mixture of 7.2 Kg NaCl in 36 L conc. $NH_3$ (12 L×3). The organic layer was concentrated to 4 V. The crude solution was slowly transferred to a stirring solution of MTBE (2400 mL, 3 V)

and n-heptane (21.6 L, 27 V) at 25° C. The flask containing the crude solution was rinsed with 800 mL anisole. Compound 3 (5 wt % seed crystal) was added. The mixture was stirred for 1 h at 25° C. and then cooled to 0° C. for 1 h with stirring. The solid was filtered, washed with n-heptane (5V) and dried in a vacuum oven at 45° C. for 16 h to give the product compound 3 (1300 g, 96.6% purity, 93.5% ee) in 80.8% yield.

Compound 3 (900 g) was dissolved in iPrOH (9 L, 10 V) and stirred for 1 h at 70° C. The solution was cooled at a rate of 10° C. every 30 min. At 35° C., racemic compound 3 (0.45 g, 0.05% wt) was added. The solution was stirred at 35° C. for 16 h. The solution was filtered, and the mother liquor was concentrated to 2.7 L (3V). The mixture was stirred at 70° C. until the solids dissolved and then cooled to 45° C. where compound 3 (9 g. 1 wt %) was added. The suspension was cooled to 35° C. where water was added dropwise (9 L, 10 V). The slurry was stirred at 25° C. for 1 h and then filtered. The solid was dried in the vacuum oven at 45° C. to give enriched compound 3 (502 g, 99.1% purity, 97.1% ee) in 55.8% yield. $^1$H NMR (400 MHz, DMSO-$d_6$) δ 9.01 (s, 1H), 7.90 (d, J=8.1 Hz, 1H), 7.69 (d, J=8.1 Hz, 1H), 5.73-5.63 (m, 1H), 5.07 (s, 1H), 5.02-4.97 (m, 1H), 4.88-4.79 (m, 2H), 4.64 (dd, J=6.1, 16.1 Hz, 1H), 3.01-2.92 (m, 1H), 2.82-2.71 (m, 1H), 2.54 (s, 3H), 2.27-2.15 (m, 1H), 2.02 (m, 1H), 1.93-1.83 (m, 1H), 1.77-1.64 (m, 1H), 0.87 (t, J=7.5 Hz, 3H); $^{13}$C NMR (101 MHz, DMSO-$d_6$) δ 175.6, 166.2, 159.3, 157.9, 154.4, 146.6, 135.4, 135.1, 131.9, 118.4, 117.9, 103.9, 80.7, 45.9, 36.5, 31.4, 26.2, 13.9, 8.3; LCMS (APCI) 384.0 [M+H]$^+$. Chiral analysis was done by HPLC on a Chiralpak ID column (4.6x250 mm), which was eluted by 0.1% DEA hexanes:ethanol, 45:55 at 1.0 mL/min. Under these conditions, the enantiomer eluted as peak 1 ($t_1$=5.62 min) and the product compound 3 eluted as peak 2 ($t_1$=9.96 min).

(R)-2-Allyl-1-(7-ethyl-7-hydroxy-6,7-dihydro-5H-cyclopenta[b]pyridin-2-yl)-64(4-(4-methylpiperazin-1-yl)phenyl)amino)-1,2-dihydro-3H-pyrazolo[3,4-d]pyrimidin-3-one (compound 1A): To a 20 L reactor was added compound 3 (750 g, 1.96 mol, 96.8% ee) and DCM (7.5 L, 10 V). The headspace was purged with $N_2$. The suspension was cooled to −5° C. and the reaction was charged with 85%, mCPBA (595.3 g, 2.93 mol) in six portions every 15 min. The reaction was stirred for 1 h at −5° C. where the initial reaction was determined to be complete by HPLC. The reaction was charged with DIPEA (1011.1 g, 2.82 mol) over 30 min. 4-(4-Methylpiperazin-1-yl)aniline (compound 4-1) (329.8 g, 2.05 mol) was then added over 45 min. The reaction was stirred between 10 to 15° C. for 7 h where it was determined to be complete by HPLC. The reaction mixture was charged with sat. $Na_2SO_3$ (3750 mL, 5 V). The temperature was maintained between 10 to 15° C. The layers were separated, and the aqueous layer was extracted with DCM (3.75 L×3, 5 V×3). The combined organic layers were washed with 20% $K_3PO_4$ (3.75 L, 5 V) and water (3.75 L, 5 V). The organic layer was concentrated to 4-5 V and iPrOH (1500 mL, 2.5 V) was added. This was repeated two times to remove DCM. iPrOH (1500 mL, 2.5 V) was added to provide a total volume of 5.6 L (7.5 V). The suspension was heated at 70° C. until all the solids dissolved. The mixture was then cooled to 40° C. over 1 h. The mixture was charged with seed crystals of compound 1A (3.75 g, 0.5% wt) at 40° C. The mixture was then cooled to 25° C. over 1 h and stirred at 25° C. for 16 h. The solids were removed by filtration and washed with n-heptane (7.5 L, 10 V). The solid was dried for 16 h at 25° C. under $N_2$ flush to give compound 1A (740 g, 99.3% purity, 97.1% ee) in 62% yield.

Example 2

Process Chemistry Route to 2-Chloro-5,6-Dihydro-7H-Cyclopenta[b]Pyridin-7-One (Compound 7)

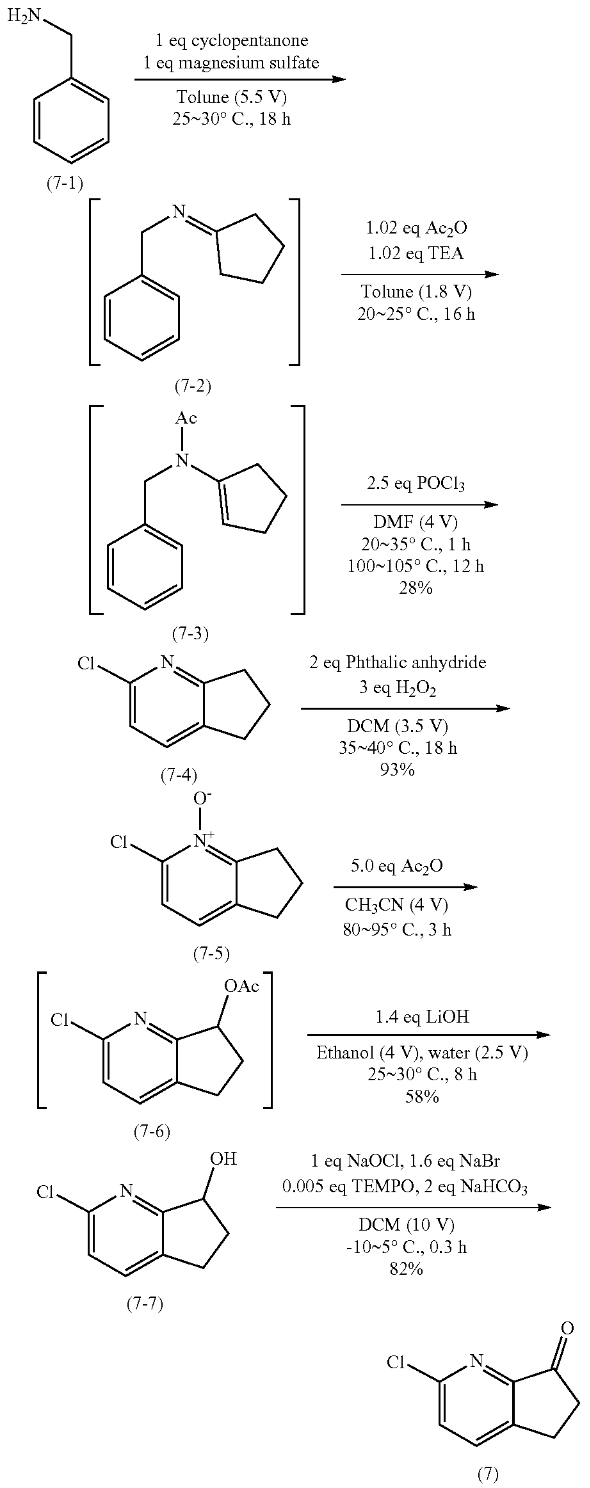

(7-1) (7-2) (7-3) (7-4) (7-5) (7-6) (7-7) (7)

2-Chloro-6,7-dihydro-5H-cyclopenta[b]pyridine (compound 7-4): A 1500 L reactor was charged with benzylamine (compound 7-1) (125.0 kg, 1167 mol), cyclopentanone (97.50 kg, 1159 mol), magnesium sulfate (140.0 kg, 1163 mol) and toluene (600 kg, 5.5 V) under $N_2$. The mixture was stirred at 25-30° C. for 18 h when the benzylamine was greater than 90% consumed by HPLC. The reaction was filtered, and the filter cake was rinsed with toluene (200 kg, 1.8 V). The filtrate was cooled to 0-10° C. with stirring. Triethylamine (120.0 kg, 1186 mol) was added to the reactor at 0-10° C. with stirring. The reactor was then charged with acetic anhydride (121.2 kg, 1187 mol) via peristaltic pump while maintaining the temperature between 0-10° C. The reaction was stirred at 20-25° C. for 16 h. The imine intermediate (compound 7-2) was >95% consumed by HPLC. The mixture was transferred to a 5000 L reactor. The organic layer was washed with water (500 L×2). The toluene was removed via distillation at 55-60° C. under vacuum. 200 L of toluene was added and removed via distillation. DMF (500 kg) was added to the reactor and the temperature was adjusted to −10-0° C. $POCl_3$ (446.3 kg, 2910 mol) was added to the reactor via peristaltic pump while maintaining the temperature between 5-15° C. The reaction was stirred at 25° C. for 1 h and then heated to 105° C. for 12 h. The mixture was cooled to 25° C. and water (500 kg) was dropwise to the mixture at 25° C. The pH was adjusted to 5 by adding 30% NaOH solution (875 kg) to the reactor. MTBE (1500 kg) was added to the reactor and the mixture was stirred for 30 min. The layers were separated, and the organic layer was filtered through Celite (20 kg). The filter cake was rinsed with MTBE (300 kg). The filtrate was washed with water (500 kg×2) and the solvent was removed at 50° C. under vacuum. Water (500 kg) was added and temperature was maintained at 20-30° C. as 36% HCl (250 kg) was added. The reaction mixture was stirred for 30 minutes and extracted with n-heptane (500 kg×2). The pH was adjusted to 10-12 by adding 30% NaOH solution while maintaining the temperature 20-30° C. The solid was collected by filtration and washed with water (300 kg). The process was repeated four times starting from 125 kg of benzylamine to give 345 kg of crude 2-chloro-6,7-dihydro-5H-cyclopenta[b]pyridine. 165 kg of crude 2-chloro-6,7-dihydro-5H-cyclopenta[b]pyridine was dissolved in n-heptane (1500 kg) and heated at 110° C. with decolorizing charcoal (10 kg) for 2 h. The mixture was cooled to 50° C., filtered and dried at 50° C. under vacuum. The solid was then slurried in ethanol (150 kg) and water (650 kg) at 20-25° C. for 30 min. The solid was removed by filtration and dried at 45° C. for 24 h to give 2-chloro-6,7-dihydro-5H-cyclopenta[b]pyridine (125 kg, 99.4% purity) as a yellow solid. 180 kg of crude 2-chloro-6,7-dihydro-5H-cyclopenta[b]pyridine was treated in the same manner as the 165 kg batch to give a total of 2-chloro-6,7-dihydro-5H-cyclopenta[b]pyridine (compound 7-4) (260 kg, 99.3% purity) as a yellow solid in 28% overall yield. $^1H$ NMR ($CDCl_3$, 400 MHz) δ 7.45 (d, J=7.8 Hz, 1H), 7.0-7.2 (m, 1H), 3.00 (t, J=7.8 Hz, 2H,), 2.91 (t, J=7.5 Hz, 2H,), 2.15 (quin, J=7.6 Hz, 2H); $^{13}C$ NMR ($CDCl_3$, 101 MHz) δ 166.5, 149.1, 135.7, 134.5, 121.1, 34.0, 30.0, 23.2; LCMS (APCI) 154.0 $[M+H]^+$.

2-Chloro-6,7-dihydro-5H-cyclopenta[b]pyridin-7-ol (compound 7-7): A 3000 L reactor was charged with 2-chloro-6,7-dihydro-5H-cyclopenta[b]pyridine (compound 7-4) (125.0 kg, 817.0 mol), DCM (576 kg), and phthalic anhydride (242.5, 1637 mol) at 25° C. with stirring. 30% Hydrogen peroxide (302.5 kg, 2696 mol) was added to the reactor. The reaction was warmed to 40° C. and stirred for 18 h where the reaction was determined to be complete HPLC. 50% $Na_2SO_3$ solution (500 kg) was added to the reaction mixture at 25° C. and stirred for 3 h. 12% $Na_2CO_3$ solution (2500 kg) was then added to adjust the pH to 8-10. The layers were separated, and the aqueous layer was extracted with DCM (750 kg×3). The combined organic layers were concentrated at 40° C. under vacuum. MTBE (375 kg) was added and concentrated to remove DCM. The crude residue was slurried with MTBE (143.7 kg) and n-heptane (350 kg) at 25° C. for 3 h. The solid was removed by filtration and dried at 30° C. under vacuum for 18 h to give 2-chloro-6,7-dihydro-5H-cyclopenta[b]pyridine 1-oxide (125 kg, 99.8% purity) as an off-white solid. This process was repeated on a 135 g batch of 2-chloro-6,7-dihydro-5H-cyclopenta[b]pyridine to provide a total of 2-chloro-6,7-dihydro-5H-cyclopenta[b]pyridine 1-oxide (compound 7-5) (258 kg, 99.8% purity) as an off-white solid in 93% yield.

Acetic anhydride (387 kg, 760.6 mol) was added to a 3000 L reactor at 25-30° C. and then warmed to 80-95° C. with stirring. 2-Chloro-6,7-dihydro-5H-cyclopenta[b]pyridine 1-oxide (compound 7-5) (129 kg, 760.6 mol) was dissolved in $CH_3CN$ (516 kg) in a 1000 L reactor. This solution was then added to the 3000 L reactor over 4 h at a temperature of 80-95° C. The reaction was stirred at 80-95° C. for 3 h where it was determined to be complete by HPLC. The $CH_3CN$ was removed via distillation and the residue was dissolved in DCM (1238 kg) followed by 13% $Na_2CO_3$ solution (1935 kg) to adjust the pH to 8-9. The layers were separated, and the aqueous layer was extracted with DCM (774 kg). The combined organic layers were concentrated.

Ethanol (412.8 kg), water (322.5 kg) and LiOH (45.15 kg, 1075 mol) were added to the crude residue at 25° C. with stirring. The reaction was stirred at 25° C. for 8 h where it was determined to be complete by HPLC. 3 N HCl solution (312.4 kg) was added to the solution to adjust the pH to 1. The mixture was filtered, and the residue washed with ethanol (103.3 kg) and water (129 kg). 30% NaOH solution (154.8 kg) was added to the mixture to adjust the pH to 9. DCM (774 kg) was added and the mixture was stirred for 30 min. The layers were separated, and the water layer was extracted with DCM (774 kg and 387 kg). The combined organic layers were stirred at 40° C. for 1 h with decolorizing charcoal (26 kg). The mixture was cooled, filtered and the DCM was removed. MTBE (290 kg) was added and then concentrated to remove DCM. The crude residue was dissolved in MTBE (50 kg) and stirred for 2 h at 20-30° C. The product was precipitated by stirring for 1 h at 0-5° C. The solid was removed by filtration, rinsed with MTBE (50 kg) and dried at 20-30° C. under vacuum for 12 h to provide 2-chloro-6,7-dihydro-5H-cyclopenta[b]pyridin-7-ol (45 kg, 98% purity) as an off-white solid. The chemistry was repeated on a second 129 kg batch of 2-chloro-6,7-dihydro-5H-cyclopenta[b]pyridine 1-oxide to provide a total of 2-chloro-6,7-dihydro-5H-cyclopenta[b]pyridin-7-ol (compound 7-7) (147 kg, 98% purity) as an off-white solid in 58% yield. $^1H$ NMR ($CDCl_3$, 400 MHz) δ 7.5-7.6 (m, 1H), 7.20 (d, J=7.9 Hz, 1H,), 5.20 (t, J=6.7 Hz, 1H), 2.9-3.1 (m, 2H), 2.7-2.9 (m, 1H), 2.5-2.6 (m, 1H), 2.0-2.2 (m, 1H); $^{13}C$ NMR ($CDCl_3$, 101 MHz) δ 165.4, 150.1, 135.8, 135.2, 123.2, 74.3, 32.8, 26.9; LCMS (APCI) 170.0 $[M+H]^+$.

2-Chloro-5,6-dihydro-7H-cyclopenta[b]pyridin-7-one (compound 7): To a 3000 L reactor was charged 2-chloro-6,7-dihydro-5H-cyclopenta[b]pyridin-7-ol (compound 7-7) (73.5 kg, 434.9 mol), $NaHCO_3$ (75.5 kg, 874.9 mol), NaBr (7.35 kg, 714.3 mol), TEMPO (0.36 kg, 2.3 mol) and DCM (955.5 kg) at 25-30° C. with stirring. The reaction mixture was cooled to −15-0° C. with stirring and the reaction was charged with 10% NaOCl (326.7 kg, 438.5 mol) dropwise. The temperature was maintained between −10-5° C. during the addition. The reaction was stirred at −10-5° C. for 30 minutes when the reaction was determined to be complete by HPLC. A 5% $Na_2SO_3$ solution (385.9 kg) was added to the reaction at 25-30° C. with stirring. The reaction was stirred for 30 min and the mixture was filtered. The filter cake was washed with DCM (147 kg). The layers were separated, and the water layer was extracted with DCM (488.7 kg). The combined organic layers were concentrated at 40° C. under vacuum. Isopropanol (146 kg) was added to the mixture and concentrated to remove residual DCM. The crude residue was slurried with MTBE (183.95 kg) and isopropanol (117.6 kg) at 50-55° C. for 2 h and then cooled to 10-20° C. The solid was removed by filtration and washed with MTBE (110.25 kg) to give 2-chloro-5,6-dihydro-7H-cyclopenta[b]pyridin-7-one (71.5 kg, wet) was a light green solid. The chemistry was repeated with a second 73.5 kg batch of 2-chloro-6,7-dihydro-5H-cyclopenta[b]pyridin-7-ol to provide a second batch of 2-chloro-5,6-dihydro-7H-cyclopenta[b]pyridin-7-one (70 kg, wet) was a light green solid. The 71.5 and 70 kg batches of 2-chloro-5,6-dihydro-7H-cyclopenta[b]pyridin-7-one were combined and triturated with MTBE (600 kg) at 20-30° C. for 2.5 h. The material was filtered and dried at 50-55° C. under vacuum to afford 2-chloro-5,6-dihydro-7H-cyclopenta[b]pyridin-7-one (compound 7) (121 kg, 99.6% purity) as an off-white solid in 82% yield. $^1H$ NMR ($CDCl_3$, 400 MHz) δ 7.86 (td, J=0.8, 8.2 Hz, 1H), 7.49 (d, J=8.1 Hz, 1H), 3.1-3.2 (m, 2H), 2.7-2.9 (m, 2H); $^{13}C$ NMR ($CDCl_3$, 101 MHz) δ 203.3, 154.2, 153.0, 148.4, 137.8, 128.5, 35.1, 23.0; LCMS (APCI) 168.0 $[M+H]^+$.

Example 3

Process Chemistry Route to 2-Allyl-6-(Methylthio)-1,2-Dihydro-3H-Pyrazolo[3,4-d]Pyrimidin-3-One (Compound 3-2)

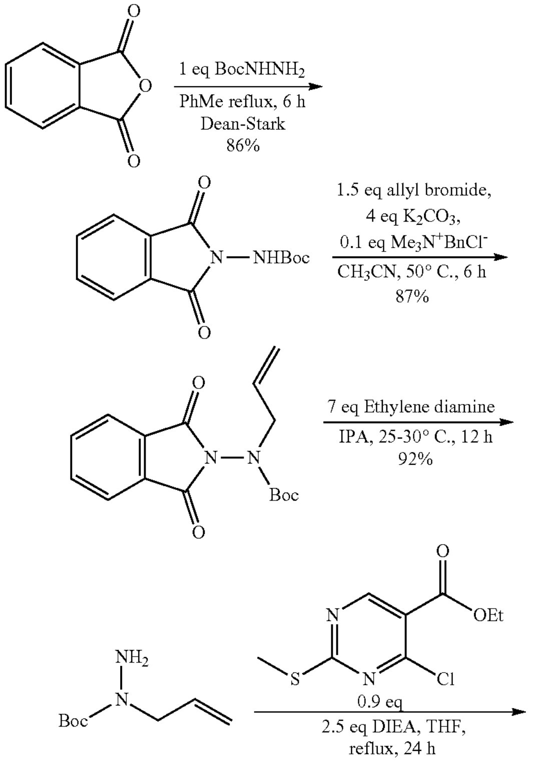

-continued

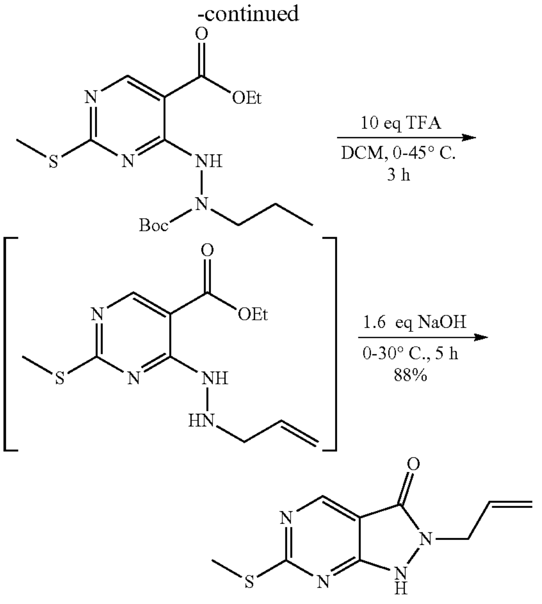

(3-2)

tert-Butyl (1,3-dioxoisoindolin-2-yl)carbamate: tert-butyl Hydrazinecarboxylate (100 kg 756.6 mol) was dissolved in dry toluene (1040 kg) in a 3000 L reactor. The reactor was charged with phthalic anhydride (106.5 kg, 719 mol) which gave a suspension. The reaction was then stirred at 100-115° C. for 6 h while utilizing a Dean-Stark apparatus to remove water. The reaction was determined to be complete by HPLC based on consumption of phthalic anhydride. The reaction was stirred for 12 h at 20-30° C. where a white precipitate formed. The precipitate was removed by filtration and washed with n-hexane (75 kg×2). The compound was dried at 25-35° C. under vacuum to provide tert-butyl (1,3-dioxoisoindolin-2-yl)carbamate (170 kg, 98.3% purity) as a white solid in 86% yield. $^1H$ NMR (DMSO-$d_6$, 300 MHz) δ 9.85 (s, 1H), 7.98-7.90 (m, 4H), 1.44 (s, 9H); MS (ESI) 207.1 $[M+H]^+$.

tert-Butyl allyl(1,3-dioxoisoindolin-2-yl)carbamate: tert-Butyl (1,3-dioxoisoindolin-2-yl)carbamate (149.5 kg 572 mol) was suspended in $CH_3CN$ (1500 kg) in a 3000 L reactor at 15-25° C. $K_2CO_3$ (317 kg, 2,294 mol) and $Me_3N^+BnCl^-$ (10.6 kg, 57.2 mol) were then added to the reactor providing a yellow suspension. Allyl bromide (103.6 kg, 858 mol) was added to the reaction. The mixture was heated to 50-55° C. with stirring for 6 h. During the reaction, the mixture became a white suspension. After 6 h, tert-butyl (1,3-dioxoisoindolin-2-yl)carbamate was consumed by HPLC. The reaction was cooled to 25-30° C. and filtered. The filter cake was washed with EtOAc (100 L). The filtrate was concentrated, and the crude material was taken up in EtOAc (600 L) and water (600 L). The layers were separated, and the water layer was extracted with EtOAc (300 L). The combined organic layers were dried ($Na_2SO_4$) and concentrated to 100 L. Hexane (500 L) was added and the mixture was concentrated. This was repeated to remove EtOAc. The residue was then triturated with hexane (300 L). The solid was collected by filtration and dried at 25° C. under vacuum to give tert-butyl allyl(1,3-dioxoisoindolin-2-yl)carbamate (150 kg, 99% purity) as a white sold in 87% yield. $^1H$ NMR (DMSO-$d_6$, 300 MHz) δ 8.02-7.93 (m, 4H), 5.93-5.78 (m, 1H), 5.26 (dd, J=17.1, 0.9 Hz, 1H), 5.17-5.10 (m, 1H), 4.18 (d, J=6.6 Hz, 2H), 1.46 & 1.25 (s, 9H); MS (ESI) 247.2 $[M+H]^+$.

tert-Butyl 1-allylhydrazine-1-carboxylate: tert-Butyl allyl (1,3-dioxoisoindolin-2-yl)carbamate (179.5 kg, 594 mol) was suspended in IPA (900 L) in a 3000 L reactor at 15-25° C. Ethane-1,2-diamine (250 kg, 4167 mol) was added to the reactor dropwise at 10-25° C. and the reaction was stirred at 15-25° C. for 16 h where it was determined to be complete by HPLC. The mixture was concentrated to 450 L and water (1,200 L) was added. The mixture was extracted with MTBE (600 L×4) and the combined organic layers were dried ($Na_2SO_4$) and the solvent removed to give tert-butyl 1-allylhydrazine-1-carboxylate (94 kg, 99% purity) as a light brown oil in 92% yield. $^1$H NMR (DMSO-$d_6$, 300 MHz) δ 5.86-5.74 (m, 1H), 5.11 (brs, 1H), 5.09-5.06 (m, 1H), 4.47 (brs, 2H), 3.89-3.81 (m, 2H), 1.40 (s, 9H).

2-Allyl-6-(methylthio)-1,2-dihydro-3H-pyrazolo[3,4-d] pyrimidin one: Ethyl 4-chloro-2-(methylthio)pyrimidine-5-carboxylate (121.8 kg, 524.7 mol) was dissolved in THF (615 kg) in a 3000 L reactor. tert-Butyl 1-allylhydrazine-1-carboxylate (99 kg, 574.2 mol) and DIPEA (168.3 kg, 1312 mol) were added giving a clear solution. The reaction was stirred for 16 h at 70-75° C. where the reaction solution became yellow. The reaction was determined to be complete by HPLC and the reaction was cooled to 25° C. The reaction was diluted with water (8 V) and extracted with EtOAc (5V×2). The combined organic layers were washed with 1 N HCl (5 V×6). The organic layers was dried ($Na_2SO_4$) and concentrated to provide ethyl 4-(2-allyl-2-(tert-butoxycarbonyl)hydrazineyl)-2-(methylthio)pyrimidine-5-carboxylate (190 kg, 98.6% purity) as a brown oil.

Ethyl 4-(2-allyl-2-(tert-butoxycarbonyl)hydrazineyl)-2-(methylthio)pyrimidine-5-carboxylate (190 kg, 516 mol) was dissolved in DCM (380 L) in a 3000 L reactor at 20° C. The reaction was cooled to −5° C. and TFA (588 kg, 5160 mol) was added to the mixture dropwise at −5-0° C. The mixture was then stirred at 25° C. for 1 h and then at 45-50° C. for 1 h. The reaction was determined to be complete by HPLC. The reaction was then cooled to 0-5° C. and 40% NaOH solution (4 V) was added to the reaction dropwise over 6 h while maintaining the temperature between 0-15° C. At pH>11 the reaction became a slurry. MeOH (5 V) was added and the reaction was stirred at 25° C. for 5 h where the reaction was determined to be complete by HPLC. The reaction mixture was concentrated to removed MeOH and DCM. 3 N HCl (12 V) was added to the residue at 0-10° C. to adjust pH<1. The solution became yellow and a solid was formed. The solid was collected by filtration and washed with water (2 V). The crude solid was suspended in water (4 V) and heated at 65-70° C. for 2 h. The mixture was cooled to 35° C. and filtered. The hot water wash was repeated three times. The material was dried under vacuum at 50-55° C. under vacuum for 48 h to provide 2-allyl-6-(methylthio)-1,2-dihydro-3H-pyrazolo[3,4-d]pyrimidin-3-one (compound 3-2) (100 kg, 99% purity) as a yellow solid in 88% yield. $^1$H NMR (DMSO-$d_6$, 400 MHz) δ 12.72 (br s, 1H), 8.66 (s, 1H), 5.8-6.0 (m, 1H), 5.0-5.2 (m, 2H), 4.38 (td, J=1.4, 5.3 Hz, 2H,), 2.5-2.5 (m, 3H); MS (ESI) 223.1 [M+H]$^+$.

Example 4

Process Chemistry Route to (R)—N-(3-Methyl-1-(pyrrolidin-1-yl)butan-2-yl)-P,P-diphenylphosphinic amide

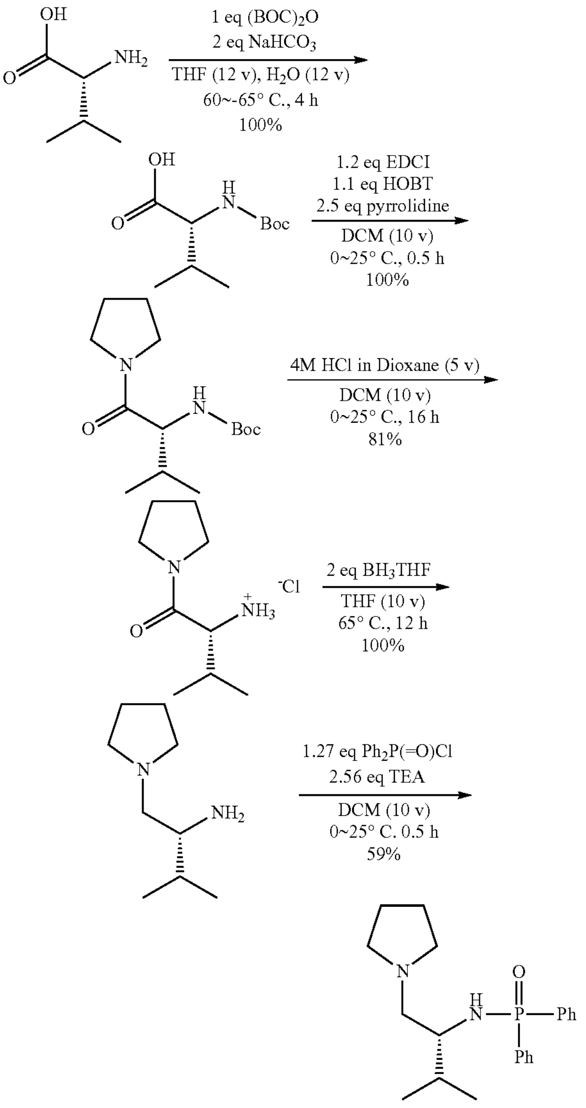

(R)-2-Amino-3-methyl-1-(pyrrolidin-1-yl)butan-1-one hydrochloride: D-Valine (78 kg, 665.8 mol), $NaHCO_3$ (111.92 kg, 1332.2 mol) and $BOC_2O$ (145.17 kg, 665.8 mol) were added to a 3000 L reactor that contains THF (830 kg) and water (935 kg). The mixture was heated to 60-65° C. with stirring for 14 h. The reaction was determined to be complete by HPLC. The mixture was concentrated under vacuum at 45° C. and the residue was dissolved in DCM (933 kg) and cooled to 5° C. 20% aq. $NaHSO_4$ (896 kg) was added to adjust the pH to 3. The mixture was stirred for 30 min and the layers were separated. The water layer was extracted with DCM (930 kg). The combined organic layers were washed with water (468 kg) and used in the next step.

A solution of (tert-butoxycarbonyl)-D-valine (665.8 mol) in DCM (1863 kg) was added to a 3000 L reactor and stirred at 20° C. HOBT (98.96 kg, 732.4 mol) and EDCI (153.2 kg, 799.2 mol) were added over 1 h and the mixture was cooled to 0° C. Pyrrolidine (118.4 kg, 1664.8 mol) was added over 3 h while maintaining the temperature between 0-11° C. The reaction mixture was stirred for 16 h at 11° C. where the reaction was determined to be compete by HPLC. 10% Citric acid (500 kg) was added and the mixture was stirred for 30 min. The layers were separated, and the organic layer was washed with 0.5 N NaOH (490 kg), water (480 kg) and dried ($MgSO_4$). The DCM layer was used directly in the next step.

The solution of tert-butyl (R)-(3-methyl-1-oxo-1-(pyrrolidin-1-yl)butan-2-yl)carbamate (665.8) in DCM (1863 kg) was added to a 3000 L reactor and cooled to 5° C. 4 M HCl in Dioxane (945 kg, 3600 mol) was added to the reaction mixture. The reaction was stirred at 15° C. for 12 h where the reaction was determined to be complete by HPLC. The reaction mixture was concentrated under vacuum at 45° C. THF (180 kg) was added and then removed by concentration under vacuum to remove residual DCM. THF (450 kg) was added and the residue was stirred at 25° C. for 17 h. The mixture was centrifuged to obtain (R)-2-amino-3-methyl-1-(pyrrolidin-1-yl)butan-1-one hydrochloride (115.8 kg, 98% purity) as white solid in 81% yield. $^1H$ NMR (400 MHz, $CDCl_3$): δ 8.43 (s, 3H), 4.19 (s, 1H), 3.86-3.82 (m, 1H), 3.64-3.57 (m, 1H), 3.43-3.38 (m, 2H), 2.34-2.30 (m, 1H), 2.03-1.82 (m, 4H), 1.16-1.14 (m, 6H). MS (ESI) 171.2 $[M+H]^+$.

(R)—N-(3-Methyl-1-(pyrrolidin-1-yl)butan-2-yl)-P,P-diphenylphosphinic amide: (R)-2-Amino-3-methyl-1-(pyrrolidin-1-yl)butan-1-one hydrochloride (46 kg, 222.53 mol) was added to a 2000 L reactor containing THF (409 kg) under $N_2$. 1 M $BH_3$ in THF (382.8 kg, 445.12 mol) was added to the reaction. The temperature increased to 38° C. during the addition. The reaction was heated to 65° C. for 16 h where the reaction was determined to be complete by HPLC. The reaction was cooled to 30° C. and MeOH (91.2 kg) was added to the solution over 2 h. The mixture was concentrated under vacuum at 45° C. DCM (184 kg) and water (138 kg) was added to the residue followed by 2 M NaOH (162.89 kg) to adjust the pH to 10. The layers were separated, and the water layer was extracted with DCM (184 kg). The combined organic layers were dried ($MgSO_4$). The DCM layer was filtered and used directly in the next step.

The solution of (R)-3-methyl-1-(pyrrolidin-1-yl)butan-2-amine (222.53 mol) in DCM (368 kg) was added to a 1000 L reactor under $N_2$ followed by TEA (52.04 kg, 514.28 mol). The solution was cooled to 0° C. and diphenylphosphinic chloride (60.1 kg, 253.98 mol) was added over 2.5 h. The reaction was stirred for 1 h where it was determined to be complete by HPLC. 10% $NaHCO_3$ (120 L) was added over 1 h and the reaction mixture was stirred for 30 min. The organic layer was separated, washed with 10% $NaHCO_3$ (120 L) and brine (120 L). The organic layer was concentrated under vacuum at 30° C. n-Heptane (52 L) was added to the residue and removed under vacuum remove residual DCM. n-Heptane (89 L) was added and the mixture was stirred for 1 h. The mixture was centrifuged to give a white solid which was then suspended in MTBE (67 kg) and stirred for 1 h. The solid was removed by centrifuge. At this point the material was combined with another second batch of (R)—N-(3-methyl-1-(pyrrolidin-1-yl)butan-2-yl)-P,P-diphenylphosphinic amide synthesized from 46 kg of (R)-2-amino-3-methyl-1-(pyrrolidin-1-yl)butan-1-one hydrochloride. The combined batches were added to MTBE (20 L) and n-heptane (200 L) and stirred for 2 h. The mixture was centrifuged to give the product (R)—N-(3-methyl-1-(pyrrolidin-1-yl)butan-2-yl)-P,P-diphenylphosphinic amide (94.3 kg, 99.2% purity, 99.9% chiral purity) as a white solid in 59% yield. 11 NMR (400 MHz, DMSO-$d_6$): δ 7.86-7.75 (m, 4H), 7.53-7.45 (m, 6H), 4.85-4.80 (m, 1H), 2.96-2.90 (m, 1H), 2.50-2.41 (m, 2H), 2.29 (s, 4H), 1.89-1.82 (m, 1H), 1.58 (s, 4H), 0.85 (d, J=7.20 Hz, 3H), 0.81 (d, J=6.80 Hz, 3H); MS (ESI) 357.3 [M+H]; $[\alpha]_D^{20}$=+10.6 (c 1.00, THF); Reported for the L-isomer$[\alpha]_D^{20}$=−9.2 (c 1.00, THF).

Example 5

Process Chemistry Route to Compound (1A)

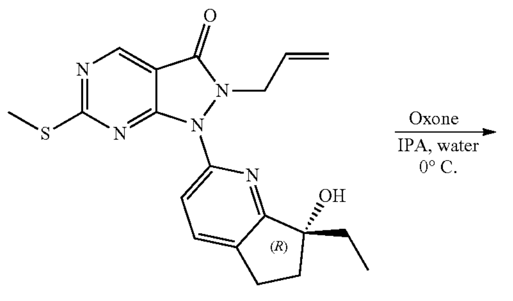

Compound 3

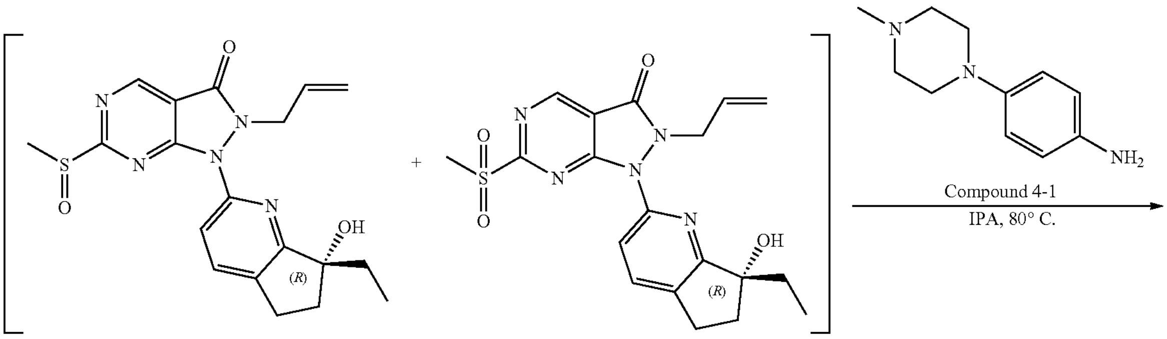

-continued

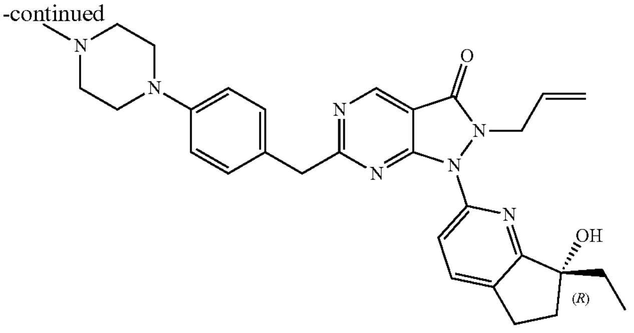

Compound 1A (R)-2-Allyl-1-(7-ethyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one (compound 1A): To a 500 L reactor was added compound 3 (7.00 kg, 18.25 mol, 96.8% ee) and isopropanol (70.0 L, 10 V). The headspace was purged with $N_2$, and the solution was cooled to −10-0° C. Oxone (9.52 kg, 15.52 mol dissolved in water 70.0 L, 10 V) was added to the mixture slowly over 5 h while maintaining a reaction temperature of −10-0° C. After complete addition, the mixture was stirred at the same temperature for another 2.5 h, where it was determined to be complete by HPLC. The mixture was charged with aqueous $NaHCO_3$ (6.30 kg, 7.49 mol dissolved in water 56.0 L, 8 V) at a temperature of −5±5° C., over 2 h until the pH was 7-8. While maintaining the same temperature, DCM (78.0 kg, 8.4 V) was added, and the mixture was stirred for 1 h. The pH of the aqueous phase was confirmed at 7-8, and an aqueous solution of $Na_2S_2O_3$ (4.55 kg of $Na_2S_2O_3{\cdot}H_2O$, 18.31 mol dissolved in water 35.0 L, 5 V) was added at a temperature of −5±5° C. over 4 h. The aqueous layer was tested with KI starch paper to confirm the quench of all the oxidant. The biphasic mixture was filtered, and the filter cake was washed with DCM (19.0 kg, 2 V). The phases were split, and the organic layer was filtered through diatomite (10.0 kg, 1.4 X). The diatomite was washed with DCM (19.0 kg, 2 V) and 4-(4-Methylpiperazin-1-yl)aniline (compound 4-1) (3.25 kg, 17.30 mol) was added. The organic layer was concentrated to 8-10 V and iPrOH (35.0 L, 5 V) was added. The mixture was concentrated to 10 V under reduced pressure at <70° C. The mixture was heated to 80±5° C., and stirred for at least 12 h, where it was determined to be complete by HPLC. The mixture was cooled to 25±5° C., and an aqueous $K_2CO_3$ solution (0.63 kg, 0.46 mol dissolved in water 21 L, 3 V) was added. The pH was adjusted to 8-10. DCM (70.0 L, 10 V) was added, and the mixture was stirred for 30 min and then let stand for 1 h. The phases were separated, and water was added to the organic layer. The mixture was stirred for 30 min, and then let stand for 1 h. DCM (14.0 L, 2 V) was added. The phases were separated, and the organic layer was filtered through a micropouous filter, which was flushed with DCM (7.0 L, 1 V). The combined organic layers were concentrated to 4-5 V under reduced pressure. IPA (35.0 L, 5 V) was added, and the mixture was concentrated to 4-5 V under reduced pressure (3×). IPA (17.5 L, 2.5 V) was added, and the mixture was heated to 70±5° C. until completely dissolved. The reactor temperature was cooled to 40±5° C. over 3 h, and seed crystals of compound 1A (35.0 g, 0.5 wt %) were added. The slurry was further stirred for 1 h at that temperature before being cooled to 0±5° C. over 4 h. The mixture was stirred at 0±5° C. for 16 h. The solids were isolated by filtration, washed with IPA (17.5 L, 2.5 V), washed with n-heptane (70.0 L, 10 V) and dried in a vacuum oven controlled at 45±5° C. with a small nitrogen flow for at least 8 h (turning over every 4-5 h). Drying was stopped when sample LOD was less than 15% to provide Compound 1A (7.23 kg, 99.3% purity, 97.1% ee) in 62% yield.

A recrystallization was performed based on the weight of the dry cake. Acetone (23.17 L, 3.2V), Compound 1A (7.24 kg, 1.0 eq.) and purified water (5.80 L, 0.8 V) were added to a 300 L reactor and warmed to 50° C. until the solid was completely dissolved. The solution was transferred to a clean 300 L reactor through a microporous in-line filter, and the reactor and filter unit were rinsed with acetone: purified water (v:v=4:1, 7.24 L, 1 V). The solution was stirred for 30 min and then cooled to 33° C. over 1 h. Seed crystals of compound 1A (65.0 g, (1-LOD) xl % wt., LOD=12%) was added in one portion at 33° C. The mixture was stirred for 5.5 h at 33° C. Purified water (21.7 L, 3 V) was added slowly to the reactor over 5.5 h, followed by additional purified water (43.4 L, 6 V) to the reactor over 2.1 h. The slurry was cooled to 4° C. over 2 h and then stirred for 8.5 h. The product was filtered and rinsed with acetone: purified water (v:v=4/10, 14.5 L, 2 V). The filter cake was placed in a vacuum oven controlled at 20° C. with a slight sweep of $N_2$ under vacuum for 16 h, then at 40° C. for 16 h to obtain compound 1A (5.98 kg, 100.00% purity, 99.6% chiral purity, 62.2% yield) as a yellow solid.

CHARACTERIZATION METHODS

XRPD Parameters

For XRPD analysis, PANalytical Empyrean X-ray powder diffractometer was used.

| Instrument | PANalytical, Empyrean |
|---|---|
| Radiation | Cu Kα (λ = 1.5418 Å) |
| Detector | PIXcel$^{1D}$ |
| Scan angle | 3-40° (2θ) |
| Scan step | 0.013° (2θ) |
| Scan speed | 20.4 s/step |
| Tube voltage/current | 45 kV/40 mA |
| Divergence slit | 1/8° |
| Rotation | On |
| Sample holder | Zero-background sample pan |

DSC Parameters

| Instrument | TA, Discovery DSC 250 |
|---|---|
| Sample pan | Aluminum, lid with pin-hole |
| Temperature range | 25-300° C. |
| Heating rate | 10° C./min |
| Purge gas | $N_2$ |
| Flow rate | 50 mL/min |

TGA Parameters

| Instrument | TA, Discovery TGA 55 |
|---|---|
| Sample pan | Aluminum, open |
| Temperature range | RT-300° C. |
| Heating rate | 10° C./min |
| Purge gas | $N_2$ |
| Flow rate | Balance chamber: 40 mL/min<br>Sample chamber: 60 mL/min |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of the following formula (3):

(3)

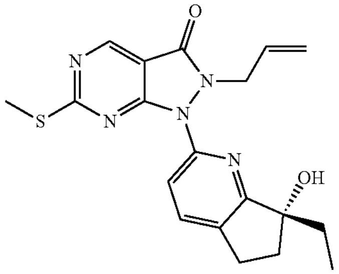

wherein formula (3) is a crystalline solid characterized by peaks in an X-ray powder diffraction pattern, wherein the peaks are about 8.6 degrees 2θ±0.2 degrees 2θ, about 11.5 degrees 2θ±0.2 degrees 2θ, about 17.3 degrees 2θ±0.2 degrees 2θ, and about 23.2 degrees 2θ±0.2 degrees 26.

2. The compound of claim 1, having an enantiomeric excess (ee) of at least 95%.

3. A method of making the compound of claim 1, comprising reacting a compound of the following formula (3-1) with a compound of the following formula (3-2) under Ullman coupling reaction conditions effective to form the compound of formula (3):

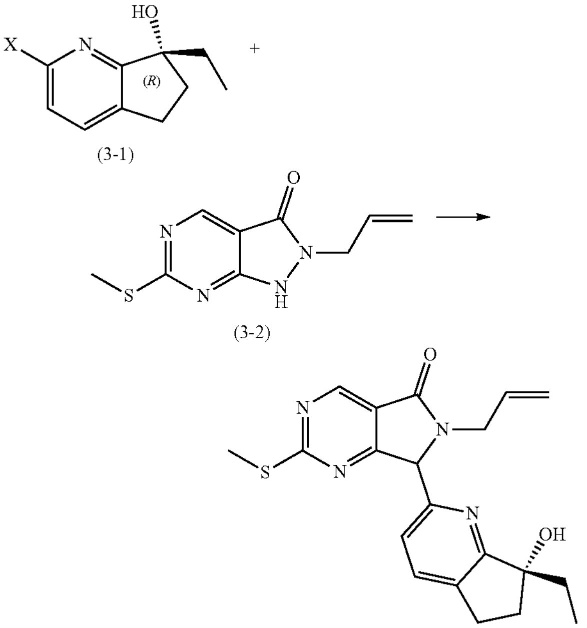

(3-1)

(3-2)

(3)

wherein X is Cl, Br or I; and wherein the Ullman coupling reaction conditions comprise reacting the compound of the formula (3-1) and the compound of the formula (3-2) together in the presence of effective amounts of a chelating ligand and NaI, wherein the chelating ligand comprises trans-N, N-dimethylcyclohexane-1,2-diamine, N,N-dimethylethane-1,2-diamine, 2,2'-bipyridyl, N,N'-dibenzylethane-1,2-diamine, trans-1,2-diaminocyclohexane or a combination thereof.

4. The method of claim 3, wherein the Ullman coupling reaction conditions comprise reacting the compound of the formula (3-1) and the compound of the formula (3-2) together in the presence of effective amounts of a polar aprotic solvent, CuI, and an inorganic base.

5. The method of claim 4, wherein the polar aprotic solvent comprises dioxane, anisole, 1,2-dimethoxyethane (glyme), diethylene glycol dimethyl ether (diglyme), dimethyl acetamide, 1-methylpyrrolidin-2-one, or a mixture thereof.

6. The method of claim 4, wherein the inorganic base comprises $K_2CO_3$, $K_3PO_4$, $Cs_2CO_3$, $Na_2CO_3$ or a combination thereof.

7. The method of claim 3, wherein the Ullman coupling reaction conditions comprise a reaction time in the range of 4 to 36 hours; and a reaction temperature in the range of about 70° C. to about 150° C.

8. The method of claim 3, wherein the method further comprises making a compound of the following formula (5), comprising:

reacting a compound of the following formula (5-1) with acetic anhydride under reaction conditions effective to form an acetyl intermediate of the following formula (5-2); and reacting the acetyl intermediate of the formula (5-2) with a hydroxide base under reaction conditions effective to form the compound of formula (5):

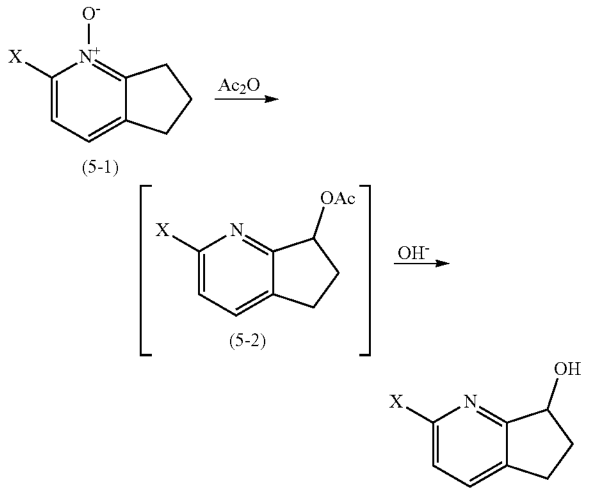

(5-1)

(5-2)

(5)

wherein X is Cl, Br or I; and wherein the hydroxide base is selected from LiOH, NaOH, KOH, $Mg(OH)_2$, $Ca(OH)_2$ and mixtures thereof.

9. The method of claim 8, wherein the reaction conditions effective to form the acetyl intermediate of the formula (5-2) comprise reacting the compound of the formula (5-1) with acetic anhydride in the presence of effective amount of an organic solvent.

10. The method of claim 8, wherein the reaction conditions effective to form the acetyl intermediate of the formula (5-2) comprise a reaction temperature in the range of about 60° C. to about 130° C.; and a reaction time in the range of 30 minutes to 10 hours; and wherein the reaction conditions effective to form the compound of formula (5) comprise a reaction temperature in the range of about 0° C. to about 50° C.; and a reaction time in the range of 2 to 24 hours.

11. The method of claim 8, wherein the reaction conditions effective to form the compound of formula (5) comprise reacting the acetyl intermediate of the formula (5-2) with the hydroxide base in the presence of an aqueous solvent that comprises a $C_{1-6}$ alcohol.

12. The method of claim 8, wherein X is Cl or I.

13. The method of claim 3, wherein the method further comprises making a compound of the following formula (6), comprising reacting a compound of the following formula (5) with an oxidizing agent under oxidizing reaction conditions effective to form the compound of formula (6):

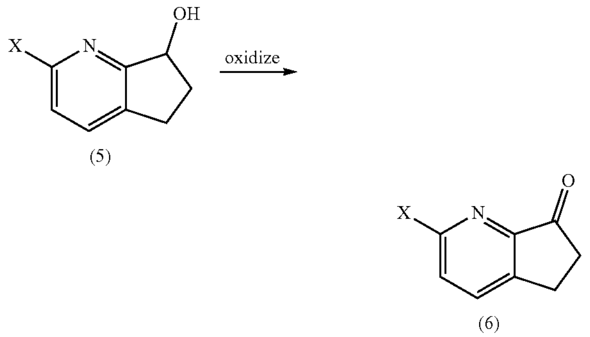

(5)

(6)

wherein X is Cl, Br or I.

14. The method of claim 13, wherein the oxidizing reaction conditions effective to form the compound of formula (6) comprise oxidizing the compound of the formula (5) with an effective amount of an oxidizing agent selected from NaOCl, NaOBr, KOCl, KOBr, $Ca(OCl)_2$ and mixtures thereof.

15. The method of claim 13, wherein the oxidizing reaction conditions effective to form the compound of formula (6) comprise mixing the compound of the formula (5) and the oxidizing agent together in a solvent; in the presence of an effective amount of (2,2,6,6-tetramethylpiperidin-1-yl)oxidanyl (TEMPO), an inorganic base, and an inorganic salt selected from LiCl, LiBr, NaCl, NaBr, KCl, KBr, and mixtures thereof; a reaction temperature in the range of about −25° C. to about 25° C.; and a reaction time in the range of 2 minutes to 4 hours.

16. The method of claim 13, wherein X is Cl or I.

17. The method of claim 3, wherein X is Cl or I.

18. A method of making a compound of the following formula (1A), comprising:

oxidizing the compound of the formula (3) of claim 1 under reaction conditions effective to form an oxidized intermediate; and reacting the oxidized intermediate with an amine compound of the following formula (4-1) under reaction conditions effective to form the compound of formula (1A):

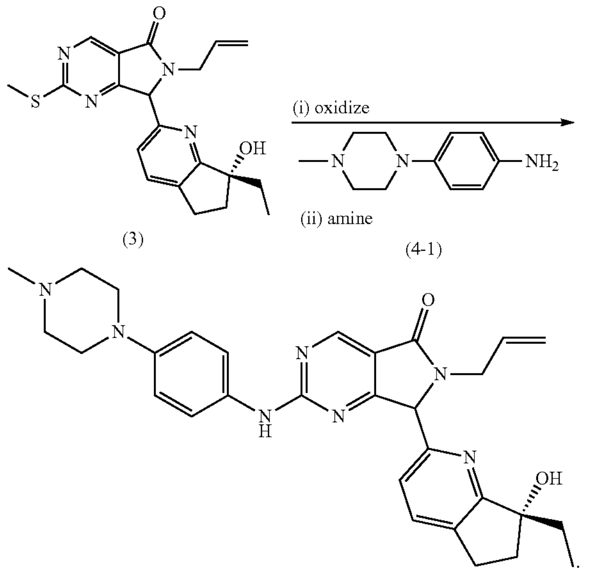

(3)

(4-1)

(1A)

19. The method of claim 18, wherein the reaction conditions effective to form the oxidized intermediate comprise oxidizing the compound of the formula (3) by reacting with an effective amount of an oxidizing agent selected from oxone, m-chloroperbenzoic acid (MCPBA), $H_2O_2$, $Na_2WO_4$, NaOCl, cyanuric acid, $NaIO_4$, $RuCl_3$, $O_2$, or a combination thereof.

20. The method of claim 18, wherein the reaction conditions effective to form the oxidized intermediate comprise oxidizing the compound of the formula (3) in the presence of effective amount of an organic solvent; a reaction temperature in the range of about −25° C. to about 25° C.; and a reaction time in the range of 30 minutes to 48 hours; and wherein the reaction conditions effective to form the compound of formula (1A) comprise a reaction temperature in the range of about 0° C. to about 50° C.; a reaction time in the range of 4 to 36 hours; and the presence of an effective amount of a base.

* * * * *